United States Patent
Kim et al.

(10) Patent No.: US 12,012,619 B2
(45) Date of Patent: Jun. 18, 2024

(54) METHODS OF USE FOR AN NADPH-REGENERATION SYSTEM BASED ON A MONOMERIC ISOCITRATE DEHYDROGENASE

(71) Applicant: INDUSTRY FOUNDATION OF CHONNAM NATIONAL UNIVERSITY, Gwangju (KR)

(72) Inventors: Geun Joong Kim, Gwangju (KR); Hun-Dong Lee, Gwangju (KR); Su-Kyoung Yoo, Gwangju (KR); Dae Eun Cheong, Gwangju (KR); Chul-Ho Yun, Sejong-si (KR); Hye-Ji Choi, Jeollanam-do (KR); Sang-Oh Ahn, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 18/054,791

(22) Filed: Nov. 11, 2022

(65) Prior Publication Data
US 2023/0143972 A1 May 11, 2023

Related U.S. Application Data

(62) Division of application No. 17/189,143, filed on Mar. 1, 2021, now abandoned.

(30) Foreign Application Priority Data

Feb. 22, 2021 (KR) .................. 10-2021-0023232

(51) Int. Cl.
*C12N 9/04* (2006.01)
*C12P 17/16* (2006.01)
*C12P 21/02* (2006.01)

(52) U.S. Cl.
CPC .......... *C12N 9/0006* (2013.01); *C12P 17/165* (2013.01); *C12P 21/02* (2013.01); *C12Y 101/01042* (2013.01); *C07K 2319/21* (2013.01)

(58) Field of Classification Search
CPC .... C12N 9/0006; C12N 9/0042; C12N 15/70; C12N 9/0069; C12P 17/165; C12P 21/02; C12P 7/02; C12P 19/36; C12Y 101/01042; C12Y 101/01041; C07K 2319/21; C07K 2319/00
See application file for complete search history.

(56) References Cited

FOREIGN PATENT DOCUMENTS

| KR | 101152878 B1 | 6/2012 |
| KR | 102022137 B1 | 9/2019 |
| WO | 2020191385 A1 | 9/2020 |

OTHER PUBLICATIONS

Peters et al., Journal of the American Chemical Society 125:13442-13450, 2003.*
Eikmanns, B. et al., "Cloning, sequence analysis, expression, and inactivation of the Corynebacterium glutamicum icd gene encoding isocitrate dehydrogenase and biochemical characterization of the enzyme," Journal of Bacteriology, vol. 177, No. 3, Feb. 1995, 9 pages.
Chen, R. et al., "A Highly Specific Monomeric Isocitrate Dehydrogenase from Corynebacterium glutamicum," Archives of Biochemistry and Biophysics, vol. 383, No. 2, Nov. 15, 2020, 8 pages.
Sahara, T. et al., "Cloning, sequencing, and expression of a gene encoding the monomeric isocitrate dehydrogenase of the nitrogen-fixing bacterium, *Azotobacter vinelandii*," Bioscience, Biotechnology, and Biochemistry, vol. 66, No. 3, Mar. 2002, 12 pages.
Wang, X. et al., "Cofactor NAD(P)H Regeneration Inspired by Heterogeneous Pathways," Chem, vol. 2, No. 5, May 11, 2017, 34 pages.
Lee, H. et al., "Expression and characterization of a recombinant isocitrate dehydrogenase in *E. coli* for cofactor regeneration," Proceedings of the KSMB 16th Annual Meeting and Symposium, Nov. 12, 2020, Yeosu, South Korea, 5 pages.
Beyer, N. et al., "P450BM3 fused to phosphite dehydrogenase allows phosphite-driven selective oxidations," Applied Microbiology and Biotechnology, vol. 101, No. 6, Mar. 2017, Available Online Nov. 29, 2016, 13 pages.
Korean Intellectual Property Office, Office Action Issued in Application No. 2021-0023232, Aug. 23, 2022, 19 pages.

* cited by examiner

*Primary Examiner* — Delia M Ramirez
(74) *Attorney, Agent, or Firm* — McCoy Russell LLP

(57) ABSTRACT

An NADPH-regeneration system based on monomeric isocitrate dehydrogenase (IDH) and a use thereof. Specifically, the present invention relates to a recombinant vector including a polynucleotide encoding an isocitrate dehydrogenase recombinant protein derived from *Corynebacterium glutamicum* (CgIDH) and an isocitrate dehydrogenase recombinant protein derived from *Azotobacter vinelandii* (AvIDH), a method for producing the recombinant protein, and an NADPH-regeneration system using the recombinant protein produced by the method. The enzyme in a monomeric form that may be efficiently used in the NADPH-regeneration system in the transformant into which the recombinant vector was introduced, was found, and the NADPH-regeneration system using the enzyme in a monomeric form has a very high utility value as biological parts and biocatalyst materials that provides NADPH to the NADPH-dependent enzyme.

6 Claims, 14 Drawing Sheets
Specification includes a Sequence Listing.

| Reaction Sample | Relative product amount (%) |
|---|---|
| BM3 | 100 |
| BM3-CgIDH | 126 |
| BM3-AvIDH | 114 |

METHODS OF USE FOR AN NADPH-REGENERATION SYSTEM BASED ON A MONOMERIC ISOCITRATE DEHYDROGENASE

CROSS REFERENCE TO RELATED APPLICATION

The present application is a divisional of U.S. Non-Provisional patent application Ser. No. 17/189,143, entitled "NADPH-REGENERATION SYSTEM BASED ON MONOMERIC ISOCITRATE DEHYDROGENASE AND USE THEREOF," and filed on Mar. 1, 2021 and now abandoned. U.S. Non-Provisional patent application Ser. No. 17/189,143 claims priority to Korean Patent Application No. 10-2021-0023232 filed on Feb. 22, 2021, now Korean Patent No. 102504343. The entire contents of each of the above-listed applications are hereby incorporated by reference for all purposes.

SEQUENCE LISTING

The instant application contains a Sequence Listing which has been filed electronically in XML format and is hereby incorporated by reference in its entirety. Said XML copy, created on Nov. 10, 2022, is named Sequence_Listing_PLS21306DIV1ST26.xml and is 17 KB in size.

TECHNICAL FIELD

The following disclosure relates to an NADPH-regeneration system based on monomeric isocitrate dehydrogenase (IDH) and a use thereof, and in particular, to an NADPH-regeneration system based on isocitrate dehydrogenase in a monomeric form, for the regeneration of NADPH, which is a cofactor used in an enzymatic reaction of an NADPH-dependent enzyme, and an application method thereof.

BACKGROUND

NADPH-dependent enzymes, for example, cytochrome P450, are a group of enzymes found in most species that function as monooxygenases.

Cytochrome P450 enzymes can mediate an oxidation reaction of a wide range of substrates, and thus, can be applied to various biosynthetic and/or degradative pathways. Cytochrome P450 enzymes not only produce high value-added biological compounds, thereby having great potential in a field of drug metabolism, but also has a very high utility value as an enzyme in industrial processes. In addition, cytochrome P450 enzymes perform an important oxidation reaction in metabolic processes of drugs or hormones, etc. in vivo, and are responsible for metabolism of greater than or equal to 75% of drugs administered to humans. Furthermore, cytochrome P450 enzymes are able to control functionality of various substrates by participating in hydroxylation reactions of the various substrates, and thus, may be widely used in the discovery of optimal metabolites or high value-added processes.

Since cytochrome P450s, especially in eukaryotes, exist typically as a membrane protein, expression and purification in foreign hosts are difficult. In addition, since most cytochrome p450s need to receive electrons from reductase, they need nicotinamide adenine dinucleotide phosphate reduced form (NADPH) as an electron transfer material. However, NADPH, which is a cofactor used in the enzymatic reaction, is highly unstable and very expensive, and there are thus may be restrictions on the industrial use of cytochrome P450s.

Meanwhile, cytochrome P450 BM3, which is a cytochrome P450 from *Bacillus megaterium*, unlike other cytochrome P450s, has an oxygenase domain involved in enzyme activity and a reductase domain that provides a reducing power required for enzyme activity through oxidation of the cofactor are not only expressed in a form of a monocistronic protein, but also expressed in cytoplasm, such that expression and purification are relatively easy. In addition, although cytochrome P450 BM3 is a multidomain protein of about 119 kDa in size, it is characterized in that a soluble overexpression in *Escherichia coli* is possible. Thus, in order to utilize cytochrome P450 BM3 as an enzyme for the industrial processes, a lot of studies for improving substrate specificity and enzyme activity, etc., are being actively conducted.

However, since NADPH, which is the cofactor of cytochrome P450, is unstable and very expensive, as described above, there is still a limitation in industrial use. In order to solve the above problems, various NADPH-regeneration systems have been developed. Specifically, the NADPH-regeneration system may use electrochemical, optical, and enzymatic methods, of which an enzymatic method is mainly used.

Examples of enzymes used in an enzyme-mediated NADPH-regeneration system include enzymes that produce NADPH in metabolic pathways in-vivo such as alcohol dehydrogenase (ADH), formate dehydrogenase (FDH), glucose dehydrogenase (GDH), and glucose 6-phosphate dehydrogenase (G6PDH).

However, all of the enzymes currently used in the NADPH-regeneration system are in a multimeric form, and have difficulties with soluble expression in *E. coli*. In particular, structural characteristics of the multimeric form have a negative influence on the enzymatic reaction, soluble expression, and upon expression of fusion protein of the NADPH-dependent enzyme such as cytochrome P450 and an enzyme used in the NADPH-regeneration system, and thus, act as a serious limiting factor in the case of producing a high value-added substance through an enzymatic process or a whole-cell reaction.

Thus, there is a need in the art for an NADPH-regeneration system capable of stably supplying NADPH to the enzymatic reaction in which the NADPH-dependent enzyme acts as a catalyst. Thus, in order to solve the problem of an enzyme used in the NADPH-regeneration system of the prior art, there is an urgent need to find an enzyme that may be used in the NADPH-regeneration system in a monomeric form, is capable of the soluble overexpression in *E. coli*, and is capable of a fusion expression with the NADPH-dependent enzyme.

RELATED ART DOCUMENT

Patent Document

Korean Patent Publication No. 2022137
Korean Patent Publication No. 1152878

Non-Patent Document

Xiaodong Wang et al., Chem., 2(5) pp. 621-654 (2017)

SUMMARY

In order to solve the problem of expensive cofactor and cofactor regeneration, which determines productivity or price of a product, in a process of developing a biocatalytic process with useful activity dependent on a cofactor using enzymes or whole-cells, an embodiment of the present disclosure is directed to providing an isocitrate dehydrogenase recombinant protein from *Corynebacterium glutamicum* and an isocitrate dehydrogenase recombinant protein from *Azotobacter vinelandii* that are solubly expressed in *E. coli* in a monomeric form and may be used in an NADPH-regeneration system, and a novel NADPH-regeneration system using the same.

In one general aspect, there is provided a recombinant expression vector for NADPH regeneration, including a polynucleotide encoding monomeric isocitrate dehydrogenase from *Corynebacterium glutamicum* or *Azotobacter vinelandii*. The recombinant expression vector may further include a polynucleotide encoding an NADPH-dependent enzyme.

The isocitrate dehydrogenase from *Corynebacterium glutamicum* may consist of an amino acid sequence of SEQ ID NO: 1 and the isocitrate dehydrogenase from *Azotobacter vinelandii* may consist of an amino acid sequence of SEQ ID NO: 2.

The NADPH-dependent enzyme may be any one or two or more selected from the group consisting of dehydrogenase, reductase, oxidoreductase, transhydrogenase, peroxidase, oxygenase, monooxygenase, flavodoxin, and dehalogenase. The NADPH-dependent enzyme may be recombined and fused to the amino acid sequence of SEQ ID NO: 1 or the amino acid sequence of SEQ ID NO: 2, or may be linked by addition of a chemical linker.

The chemical linker may be selected from the group consisting of PEGylated bis(sulfosuccinimidyl) suberate (BS(PEG)5), PEGylated bis(sulfosuccinimidyl) suberate (BS(PEG)9), bis(sulfosuccinimidyl) glutarate-d0 (BS2G-d0), bis(sulfosuccinimidyl) 2,2,4,4-glutarate-d4 (BS2G-d4), di succinimidyl dibutyric urea (DSBU), 1,5-difluoro-2,4-dinitrobenzene (DFDNB), dimethyl pimelimidate (DMP), dimethyl suberimidate (DMS), disuccinimidyl glutarate (DSG), dithiobis(succinimidyl) propionate (DSP), di succinimidyl suberate (DSS), disuccinimidyl sulfoxide (DSSO), disuccinimidyl tartarate (DST), dimethyl-3,3-dithiobis propionimidate (DTBP), ethylene glycol bis(succinimidyl) succinate (EGS), tris-(succinimidyl) aminotriacetate (T SAT), and 1-ethyl-3-(3-dim ethyl aminopropyl) carbodiimide (EDC).

The present invention provides a transformant transformed with the recombinant expression vector for NADPH regeneration. The transformant may be *Escherichia coli*.

In another general aspect, there is provided a method for producing a recombinant protein including: producing the recombinant expression vector for NADPH regeneration as described above; transforming the recombinant expression vector to produce a transformant; culturing the transformant to overexpress isocitrate dehydrogenase from *Corynebacterium glutamicum* or isocitrate dehydrogenase from *Azotobacter vinelandii*; and recovering the overexpressed recombinant protein. The culturing may be performed at 28 to 32° C.

The present invention provides a recombinant protein produced by the method for producing a recombinant protein. The recombinant protein may be solubly expressed in a monomeric form, and may be used together with the NADPH-dependent enzyme. The NADPH-dependent enzyme may be any one or two or more selected from the group consisting of dehydrogenase, reductase, oxidoreductase, transhydrogenase, peroxidase, oxygenase, monooxygenase, flavodoxin, and dehalogenase. The NADPH-dependent enzyme may be recombined and fused to the amino acid sequence of SEQ ID NO: 1 or the amino acid sequence of SEQ ID NO: 2, or may be linked by addition of a chemical linker.

The chemical linker may be selected from the group consisting of BS(PEG)5, BS(PEG)9, BS2G-d0, BS2G-d4, DSBU, DFDNB, DMP, DMS, DSG, DSP, DSS, DSSO, DST, DTBP, EGS, TSAT, and EDC.

The present invention provides a composition for NADPH regeneration, comprising the recombinant protein.

The present invention provides a method for regenerating NADPH including: regenerating NADPH by adding the recombinant protein to an NADPH-dependent enzyme reaction system.

The present invention provides a kit for NADPH regeneration, including the recombinant protein.

In another general aspect, there is provided a composition for substrate hydroxylation, comprising the recombinant protein; and a cytochrome P450 protein. The substrate may be selected from the group consisting of omeprazole, omeprazole sulfide, ethoxycoumarin, and nitrophenol.

The present invention provides an in vitro toxicity test method including: treating the composition for substrate hydroxylation.

The present invention provides a method for converting a target substrate by co-expressing or fusion expressing the recombinant isocitrate dehydrogenase protein and the NADPH-dependent enzyme.

Other features and aspects will be apparent from the following detailed description and the drawings.

DETAILED DESCRIPTION

Hereinafter, an NADPH-regeneration system based on monomeric isocitrate dehydrogenase of the present invention and a use thereof will be described in detail with reference to the accompanying table or drawings.

If the drawings are described, they are provided as examples so that the spirit of the present invention can be sufficiently transferred to those skilled in the art. Therefore, the present invention is not limited to the accompanying drawings, but may be modified in many different forms. In addition, the accompanying drawings described below will be exaggerated in order to illustrate the spirit and scope of the present invention.

Terms such as "first", "second", etc. may be used to describe various components, but these components are not to be construed as being limited to these terms. The terms are used only to distinguish one component from another component. For example, a first component may be referred to as a second component and the second component may also be similarly referred to as the first component, without departing from the scope of the present invention.

Technical terms and scientific terms used in the present specification have the general meaning understood by those skilled in the art to which the present invention pertains unless otherwise defined, and a description for the known function and configuration unnecessarily obscuring the gist of the present invention will be omitted in the following description and the accompanying drawings. Terms generally used and defined by a dictionary should be interpreted as having the same meanings as meanings within a context of the related art and should not be interpreted as having ideal or excessively formal meanings unless being clearly defined otherwise in the present specification.

In addition, singular forms used in the specification of the present invention are intended to include the plural forms as well unless otherwise indicated in context.

Further, units used in the specification of the present invention without special mention are by weight, and as an example, the unit of % or ratio means % by weight or a ratio by weight, respectively.

Furthermore, in the specification of the present invention, the expression "comprise" is an "open" description having the meaning equivalent to expressions such as "include," "contain," "have," or "feature", and does not exclude elements, materials, or processes that are not further listed. In addition, the expression "substantially composed of . . . " means that other elements, materials, or processes not listed with the specified element, material or process may be present in an amount that does not have an unacceptably significant effect on at least one basic and novel technical idea of the invention. Further, the expression "composed of" means that only the described elements, materials, or processes are present.

Figure 1:
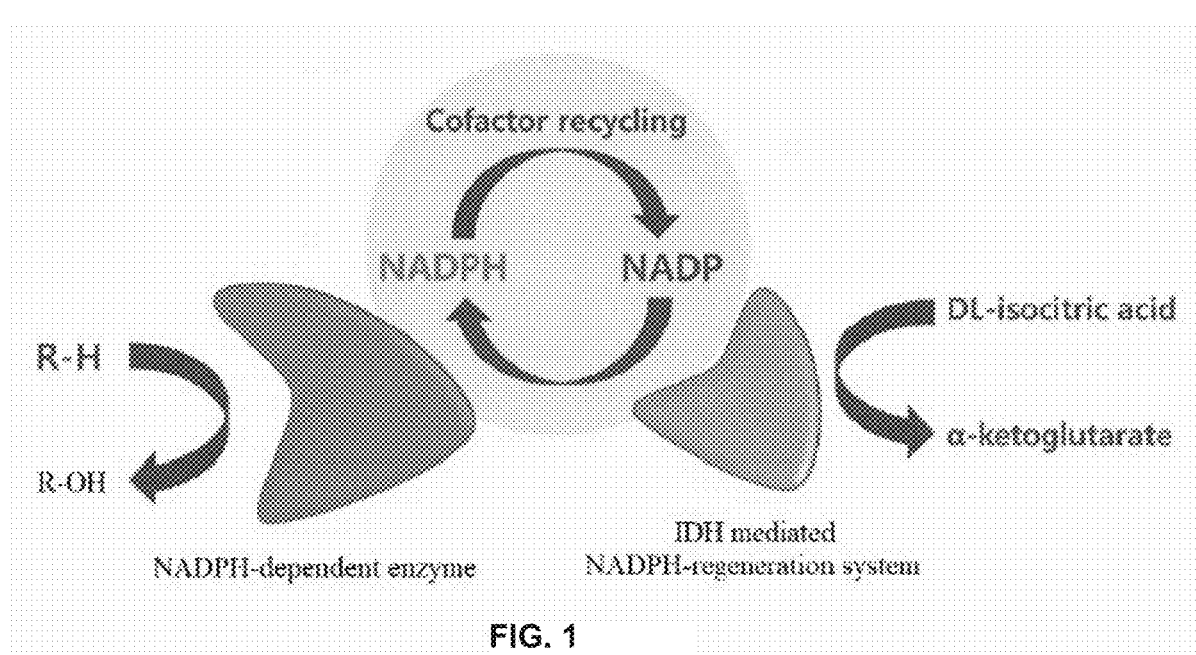
FIG. 1 is a schematic diagram illustrating an NADPH-regeneration system based on isocitrate dehydrogenase in a monomeric form according to the present invention.

In the specification of the present invention, "NADPH regeneration" is meant to include not only a process of recycling NADPH together with an NADPH-dependent enzyme by converting $NADP^+$ produced by the NADPH-dependent enzyme into NADPH, but also a reaction of producing NADPH from free $NADP^+$, as can be seen in FIG. 1, unless otherwise specified.

In the specification of the present invention, the term "vector", "expression vector", or "recombinant expression vector" is a linear or circular DNA molecule that encodes an operably linked polynucleotide, comprising elements and additional fragments that provide for gene transcription and translation. Additional fragments include a promoter, a transcription termination sequence, etc. A vector, an expression vector, or a recombinant expression vector includes one or more origins replication, one or more selection markers, etc. A vector, an expression vector, or a recombinant expression vector is generally derived from plasmid or viral DNA, or contains elements of both of them.

In the specification of the present invention, the term "recombination protein" refers to a conventional expression protein that expresses a gene from a cell of another species using a heterologous host, but includes a protein to which another protein is linked or a different amino acid sequence is added to an amino or carboxyl terminus of a target protein sequence, if necessary. In the present invention, an affinity tag may be further included at the carboxyl terminus of a recombinant protein of isocitrate dehydrogenase from *Corynebacterium glutamicumr* (CgIDH) and a recombinant protein of isocitrate dehydrogenase from *Azotobacter vinelandii* (AvIDH) for ease of purification. A histidine tag (his-tag) may be used as the affinity tag, but is not limited thereto.

A recombinant expression vector for NADPH regeneration according to the present invention includes a polynucleotide encoding an isocitrate dehydrogenase recombinant protein (CgIDH or AvIDH) monomer from *Corynebacterium glutamicum* or *Azotobacter vinelandii*. Here, the recombinant expression vector may preferably be one such that the recombinant protein monomer is solubly overexpressed, but is not limited thereto.

The isocitrate dehydrogenase from *Corynebacterium glutamicum*, as a specific example, may consist of an amino acid sequence of SEQ ID NO: 1 and the isocitrate dehydrogenase from *Azotobacter vinelandii* may consist of an amino acid sequence of SEQ ID NO: 2.

The polynucleotide is not particularly limited as long as it is a nucleic acid sequence capable of encoding CgIDH or AvIDH. For example, the polynucleotide encoding CgIDH may consist of, but is not limited to, a nucleic acid sequence of SEQ ID NO: 7, and the polynucleotide encoding AvIDH may consist of a nucleic acid sequence of SEQ ID NO: 8. The polynucleotide may be operably linked to the promoter to ensure that the expression of the protein is well achieved when introduced into a recombinant expression vector.

Here, the term "operably linked" refers to a state in which a nucleic acid expression control sequence and a nucleic acid sequence encoding a target protein or RNA are functionally linked to perform a general function. For example, the nucleic acid sequence encoding the protein or RNA is operably linked with the promoter, which can affect the expression of the coding sequence. An operable linkage with the expression vector may be produced by gene recombination techniques well known in the art, and site-specific DNA cleavage and linkage may be used by appropriately introducing enzymes or homologous gene recombination techniques, etc. generally known in the art.

The promoter may be derived from, but is not limited to, a subject (host) to which a recombinant vector of the present invention is to be introduced, and examples of thereof include a T7 promoter.

In the transformant into which the recombinant vector was introduced, CgIDH and/or AvIDH are/is expressed from the polynucleotide encoding CgIDH and/or the polynucleotide encoding AvIDH.

The recombinant vector of the present invention may be, but is not limited to, a plasmid vector, a cosmid vector, a bacteriophage vector, a viral vector, etc. as template. A preferred example thereof may include a promoter, an operator, an initiation codon, a stop codon, an expression control element such as a polyadenylation signal and an enhancer, etc., and may be prepared in various ways according to the purpose. The recombinant vector may include an antibiotic resistance marker for selection of transformants into which the vector was introduced, which may be inherent in the vector or may be introduced from the outside.

In the recombinant expression vector for NADPH regeneration according to an embodiment of the present invention, the recombinant expression vector may further include a polynucleotide encoding the NADPH-dependent enzyme. A specific example of the NADPH-dependent enzyme may be, but is not limited to, any one or two or more selected from the group consisting of dehydrogenase, reductase, oxidoreductase, transhydrogenase, peroxidase, oxygenase, monooxygenase, flavodoxin, and dehalogenase, preferably dehydrogenase.

In the recombinant expression vector for NADPH regeneration according to an embodiment of the present invention, the NADPH-dependent enzyme may be recombined and fused to the amino acid sequence of SEQ ID NO: 1 or the amino acid sequence of SEQ ID NO: 2, or may be linked by addition of a chemical linker.

In the recombinant expression vector for NADPH regeneration according to an embodiment of the present invention, the chemical linker may be selected from the group consisting of BS(PEG)5, BS(PEG)9, BS2G-d0, BS2G-d4, DSBU, DFDNB, DMP, DMS, DSG, DSP, DSS, DSSO, DST, DTBP, EGS, TSAT, and EDC.

The present invention provides a transformant transformed with the recombinant expression vector for NADPH regeneration. The type of the transformant is not limited as long as the recombinant expression vector of the present invention can be introduced to express CgIDH and/or AvIDH. Examples of the transformant may be selected from strains included in genus *Escherichia*, genus *Salmonella*, genus *Shigella*, genus *Enterobacter*, genus *Proteus*, genus *Pseudomonas*, genus *Moraxella*, genus *Helicobacter*, genus *Stenotropomonas*, genus Bdellovibrio, genus *Legionella*, genus *Neisseria*, and genus *Erwinia*. Specific examples of the transformant may be *E. coli*, and more specifically, *E. coli* BL21 (DE3).

When the transformant is produced, a transformation method may be performed by conventional methods in the art, for example, but is not limited to, a natural introduction method, a heat shock method, an electric shock method, etc.

The present invention provides a method for producing a recombinant protein including culturing the transformant, and more specifically, the method for producing the recombinant protein includes producing the recombinant expression vector for NADPH regeneration as described above; transforming the recombinant expression vector to produce a transformant; culturing the transformant to overexpress isocitrate dehydrogenase originated from *Corynebacterium glutamicum* or isocitrate dehydrogenase derived from *Azotobacter vinelandii*; and recovering the overexpressed recombinant protein.

Culture conditions are not particularly limited when the transformant is cultured, but may be used by introducing known culture conditions. As a specific example, the culture may be performed at 28 to 32° C., preferably 29 to 31° C., and more preferably 30° C., and the soluble expression of 90% or more of the target protein may be implemented in the culture temperature range described above. A medium for culturing microorganisms may also be appropriately introduced and used into a known medium, and as a specific example, a Luria-Bertani (LB) medium may be used, but is not limited thereto.

When the transformant expresses the recombinant protein by the introduction of the recombinant expression vector, the culture medium may further contain an appropriate antibiotic for selection of a transformed microorganism, and may further contain a substance for promoting expression of the recombinant protein, for example, but is not limited to, isopropyl β-D-1-thiogalactopyranoside (IPTG), etc., if necessary.

The method for producing the recombinant protein may be obtained by separating and purifying the recombinant protein from the culture of the transformant, wherein the culture may be the transformant or a culture medium thereof, and the culture medium may be a medium containing the transformant or a medium obtained by separating the transformant.

In addition, for easy separation and purification of the recombinant protein, the transformant may be destroyed, and as specific methods of destruction, methods, such as, but is not limited to, physical destruction through ultrasonic decomposition or chemical destruction through a non-ionic detergent (surfactant), etc., may be used.

In addition, the method for preparing the recombinant protein may further include isolating and purifying CgIDH and/or AvIDH, and the isolating and purifying may be performed by introducing conventional separation and purification processes in the art, which is performed to utilize the expressed protein for desired purpose or use. Through such separation and purification processes, a high yield of recombinant protein may be obtained.

The present invention provides a method for regenerating NADPH, including regenerating NADPH by adding the recombinant protein to an NADPH-dependent enzyme reaction system, an NADPH-regeneration system, and a method for regenerating NADPH, which is the cofactor of the NADPH-dependent enzyme, such as cytochrome P450.

Specific examples of the NADPH-dependent enzyme may be, but are not limited to, any one or two or more selected from the group consisting of dehydrogenase, reductase, oxidoreductase, transhydrogenase, peroxidase, oxygenase, monooxygenase, flavodoxin, and dehalogenase, preferably dehydrogenase.

The NADPH-dependent enzyme may be recombined and fused to CgIDH and/or AvIDH, or may be linked by a chemical linker. The chemical linker may be selected from, but is not limited to, the group consisting of BS(PEG)5, BS(PEG)9, BS2G-d0, BS2G-d4, DSBU, DFDNB, DMP, DMS, DSG, DSP, DSS, DSSO, DST, DTBP, EGS, TSAT, and EDC.

The present invention provides a kit for NADPH regeneration, including the recombinant protein.

In addition, the present invention provides a composition for substrate hydroxylation comprising the recombinant protein; and a NADPH dependent cytochrome P450 protein.

Here, the recombinant protein may refer to, but is not limited to, a NADPH regeneration-related construct (system) including the same. Specific examples of the substrate may be selected from, but is not limited to, the group consisting of omeprazole, omeprazole sulfide, ethoxycoumarin, and nitrophenol.

The composition for substrate hydroxylation not only may include an NADPH-regeneration system using CgIDH and/or AvIDH to provide expensive NADPH used for cytochrome P450, but may also be used as a biological catalyst for a hydroxylation reaction of a wide range of substrates including cytochrome P450 protein by genetic fusion.

The present invention provides an in vitro toxicity test method including treating the composition for substrate hydroxylation. Here, the type of toxicity test is not particularly limited, but may include a drug toxicity test, a liver toxicity test, etc.

The present invention provides a method of converting a target substrate by co-expressing or fusion expressing the recombinant isocitrate dehydrogenase protein and the NADPH-dependent enzyme.

Hereinafter, the content of the present invention will be described in more detail through examples. The examples are only for describing the present invention in more detail, and the scope of the present invention is not limited thereto.

Strain, Reagent, Material, and Experimental Protocol

In the present invention, reagents, materials, and protocols used for polymerase chain reaction (PCR), DNA cloning, transformation, etc. are as follows, which will be apparent to those skilled in the art.

*Corynebacterium glutamicum* ATCC13032 was obtained from the American Type Culture Collection (ATCC, USA), an international depository organization, and used.

*Azotobacter vinelandii* KACC10899 was obtained from the Korean Agricultural Culture Collection (KACC, Korea), and used.

*E. coli* XL1-Blue was purchased from Yeastern Biotech. (Taiwan), and used.

*E. coli* BL21 (DE3) was purchased from Yeastern Biotech. (Taiwan), and used.

pET24a plasmid was purchased from New England Labs (UK), and used.

A PureLink™ Genomic DNA Kit was purchased from Thermo Fisher Scientific Korea (Korea), and used.

Primers for gene amplification were synthesized by BIONICS (Korea), and used.

Speed-Pfu DNA Polymerase was purchased from Nano-Helix Co., Ltd. (Korea), and used.

An In-Fusion®HD cloning kit was purchased from Takara Korea Biomedical Inc., and used.

Other NdeI and XhoI restriction enzymes were purchased from Takara Korea Biomedical Inc. (Korea), and used.

The other reagents were purchased from Sigma-Aldrich (USA), etc., and used.

Transformant

*E. coli* XL1-Blue was used as the transformant for plasmid transformation and genetic manipulation.

*E. coli* BL21 (DE3) was used as the transformant for protein expression.

Histidine Tag (His-Tag)

Since fusion of a histidine tag to an amino terminus (N-terminus) of a recombinant protein may affect the expression and the structure of a whole protein in some cases, primers were synthesized so that the histidine tag is fused to a carboxyl terminus (C-terminus).

Example 1

Construction of Recombinant Vector for Overexpression and Production of Recombinant Protein Plasmid construction was performed based on standard DNA manipulation techniques. First, a PureLink™ Genomic DNA Kit was used to extract each genomic DNA from *Corynebacterium glutamicum* ATCC13032 and *Azotobacter vinelandii* KACC10899. Thereafter, PCR was performed using the extracted genomic DNA as templates.

Here, for the PCR reaction, primers composed of each sequence in Table 1 below were each synthesized and used.

TABLE 1

| SEQ ID No. | Primer name | Sequence (5'→3') | Restriction enzyme |
| --- | --- | --- | --- |
| 3 | CgIDH infusion F | 5'-GAA GGA GAT ATA CAT ATG GCT AAG ATC ATC TGG ACC CG-3' | NdeI |
| 4 | CgIDH infusion R | 5'-GTG GTG GTG GTG CTC GAG CTT CTT CAG TGC GTC AAC GAT CTC-3' | XhoI |
| 5 | AvIDH infusion F | 5'-GAA GGA GAT ATA CAT ATG TCC ACA CCG AAG ATT ATC TAT ACG C-3' | NdeI |
| 6 | AvIDH infusion R | 5'-GTG GTG GTG GTG CTC GAG TGC AAG AGG TGC CAG AGC C-3' | XhoI |

Using primers of SEQ ID NOs: 3 and 4 with the template of genomic DNA extracted from *Corynebacterium glutamicum* ATCC13032, polynucleotide 1 encoding an isocitrate dehydrogenase protein from *Corynebacterium glutamicum* (CgIDH) was amplified by PCR. Using primers of SEQ ID NOs: 5 and 6 with the template for genomic DNA extracted from *Azotobacter vinelandii* KACC10899, polynucleotide 2 encoding an isocitrate dehydrogenase protein from *Azotobacter vinelandii* (AvIDH) was amplified in the same manner. During the PCR amplification, a Speed-Pfu DNA polymerase, which is a polymerase having a low mutation frequency, was used.

DNA fragments obtained through PCR were cloned into pET24a plasmids treated with NdeI and XhoI restriction enzymes, respectively, using an In-Fusion® HD cloning kit. The results are shown in FIGS. 2A and 2B.

Figure 2A:
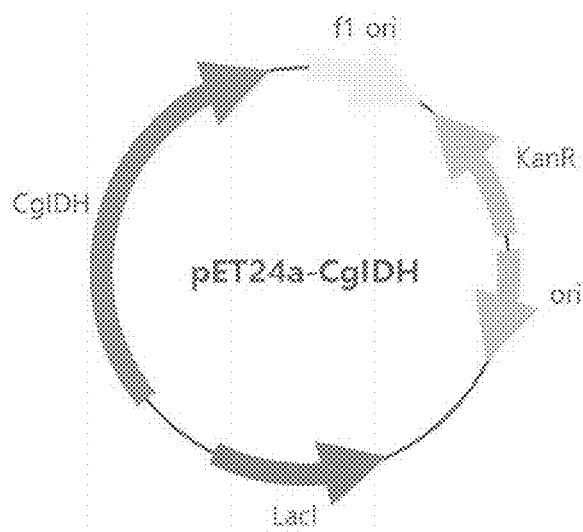
FIGS. 2A and 2B illustrate schematic diagrams of the recombinant vector for expressing a recombinant protein of isocitrate dehydrogenase from *Corynebacterium glutamicum* (hereinafter may be referred to as CgIDH) and a recombinant protein of isocitrate dehydrogenase from *Azotobacter vinelandii* (hereinafter may be referred to as AvIDH)
Figure 2B:
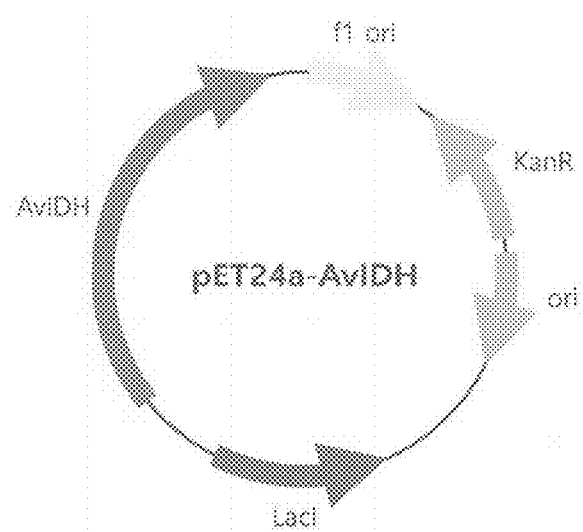

Each of FIGS. 2A and 2B illustrates schematic diagrams of the recombinant vector for transcribing and translating genes (cgIDH and avIDH) encoding amino acid sequences of SEQ ID NO: 1 and SEQ ID NO: 2, under the control of a T7 promoter.

Example 2

Establishment of Expression Conditions and Purification of Recombinant Protein

Establishment of Expression Conditions of Recombinant Protein

In order to provide high expression conditions for purification of the recombinant protein, the expression conditions were established while confirming an expression pattern of the IDH protein.

The recombinant expression vectors, pET24a-CgIDH and pET24a-AvIDH constructed in Example 1 above were transformed into *E. coli* XL1-Blue, respectively, using a method that is apparent to those skilled in the art, plated on an LB solid medium containing 50 ug/mL kanamycin, and then cultured overnight at 37° C. Then, *E. coli* XL1-Blues into which the recombinant expression vectors were introduced, were each inoculated into an LB liquid medium containing 50 ug/mL of kanamycin, and the recombinant expression vectors were purely isolated from the harvested bacteria by centrifuging the cultured bacteria at 220 rpm at 37° C.

The recombinant expression vectors isolated through the above process were each transformed into *E. coli* BL21 (DE3), plated on the LB solid medium containing 50 ug/mL of kanamycin, and then cultured overnight at 37° C. Thereafter, a single clone grown in the medium was inoculated into the LB liquid medium containing 50 ug/mL of kanamycin, and then absorbance ($OD_{600}$) was measured at 600 nm while being pre-cultured at 220 rpm at 37° C.

When the absorbance of a culture solution reached 2.0 to 2.5, after passage to the LB liquid medium having the same composition, the culturing was performed until the absorbance reached 0.6. Thereafter, 100 mM IPTG was added so that a final concentration was 0.2 mM, and the medium was incubated for further 2.5 hours at 220 rpm at 37° C. and 30° C. After completion of the culture cells were harvested by centrifugation and then adjusted to be 2.0 of $OD_{600}$ for complete washing with DDW.

The cells were resuspended in 200 uL of 1× phosphate-buffered saline (PBS, pH 7.4), and then disrupted by sonication. Immediately after crushing, the whole protein fractions were taken and centrifuged at 16,000×g at 4° C. for 30 minutes to remove insoluble aggregates, and aliquoted soluble fractions.

To the samples taken in each step, 5× sample loading buffer (0.225 M Tris-HCl pH 6.8, 50% glycerol, 5% SDS, 0.005 M bromophenol blue, and 0.25 M dithiothreitol (DTT)) was added in a ratio of 5:1, and the resulting samples was heated at 95° C. for 15 minutes to induce denaturation of the whole proteins. Then, after slowly cooling each sample, the prepared sample was loaded on a 10% acrylamide gel and fixed at 150V, followed by electrophoresis. After completion of the electrophoresis, the acrylamide gel was stained with a Coomassie Brilliant Blue solution, and expression patterns of CgIDH and AvIDH depending on culture temperature were compared and shown in FIGS. 3A and 3B.

Figure 3A:
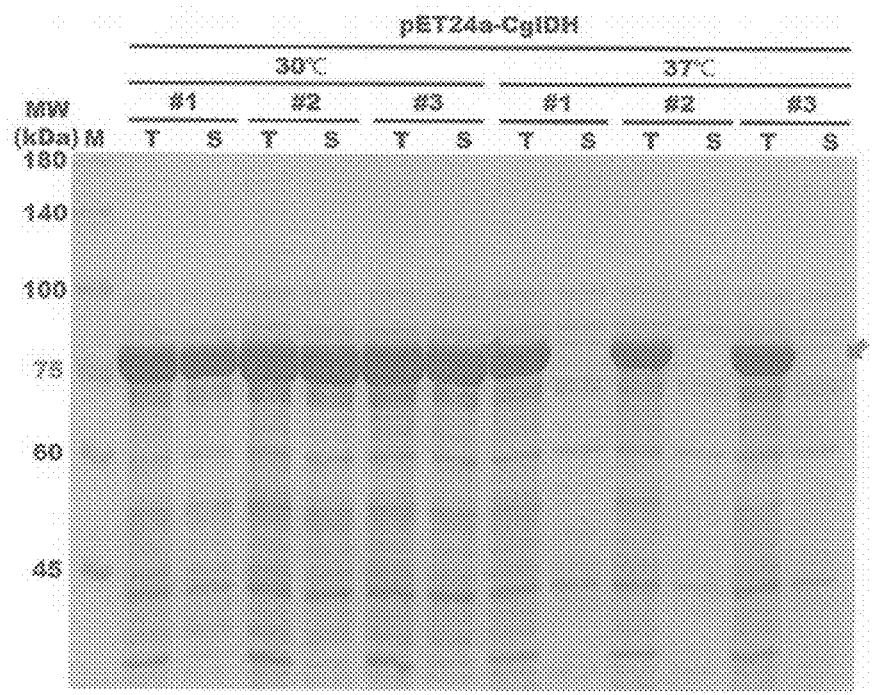
FIGS. 3A and 3B are each a SDS-PAGE analysis result depending on an expression temperature of CgIDH and AvIDH.
Figure 3B:
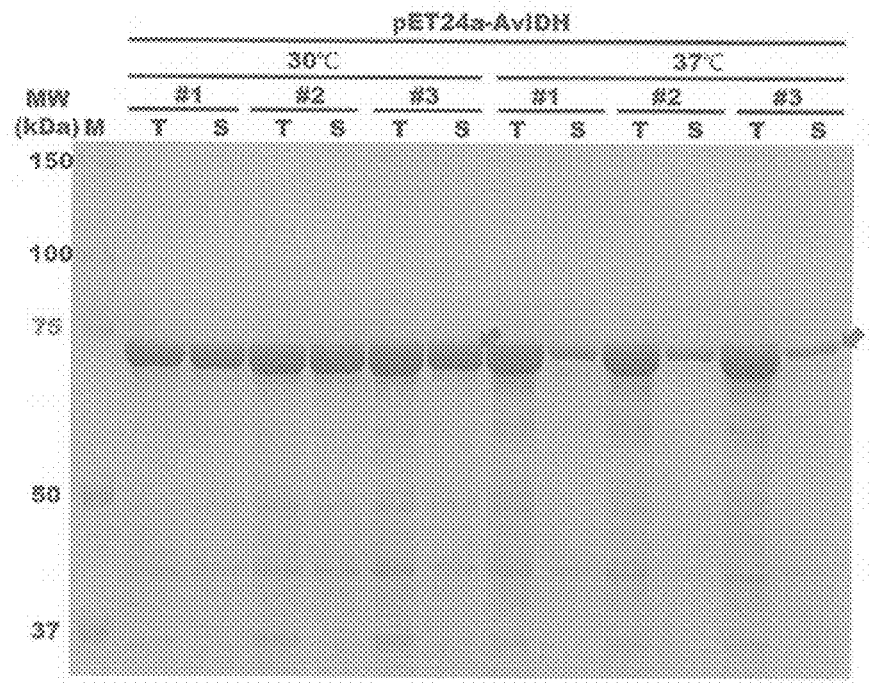

Each of FIGS. 3A and 3B is the SDS-PAGE analysis result for confirming the expression patterns after expressing CgIDH and AvIDH in *E. coli* BL21 (DE3) under differently set induction temperate at 30° C. and 37° C., respectively. As a result, when CgIDH was expressed at 30° C., a soluble overexpressed band was confirmed at a position of about 80 kDa, and when AvIDH was expressed at 30° C., a soluble overexpressed band was confirmed at a position of about 70 kDa. It was confirmed from these results that soluble expression did not occur when the expression temperature of both of the recombinant proteins was set to 37° C., but 90% or more soluble expression was achieved when the expression temperature was set to 30° C.

Purification of Recombinant Protein

For the purification of the protein expressed as described above, after increasing culture volume to 100 mL, the culturing was performed in the same procedure as the above culture method.

Each of the cells harvested by the procedure as described above was resuspended by adding 40 mL of 60 mM potassium phosphate buffer (pH 7.7) containing 300 mM sodium chloride. The resuspended cells were destroyed by sonication, and centrifuged at 16,000×g at 4° C. for 60 minutes to separate supernatant from which the insoluble aggregates were removed. Thereafter, 40 mL of soluble protein solutions were each loaded onto a 5 mL Histrap column (GE Healthcare Life Science, USA). After completion of loading of each of soluble protein fractions, they were sufficiently washed with the same buffer, and the recombinant protein was eluted by gradient to a concentration of 250 mM imidazole.

Figure 4A:
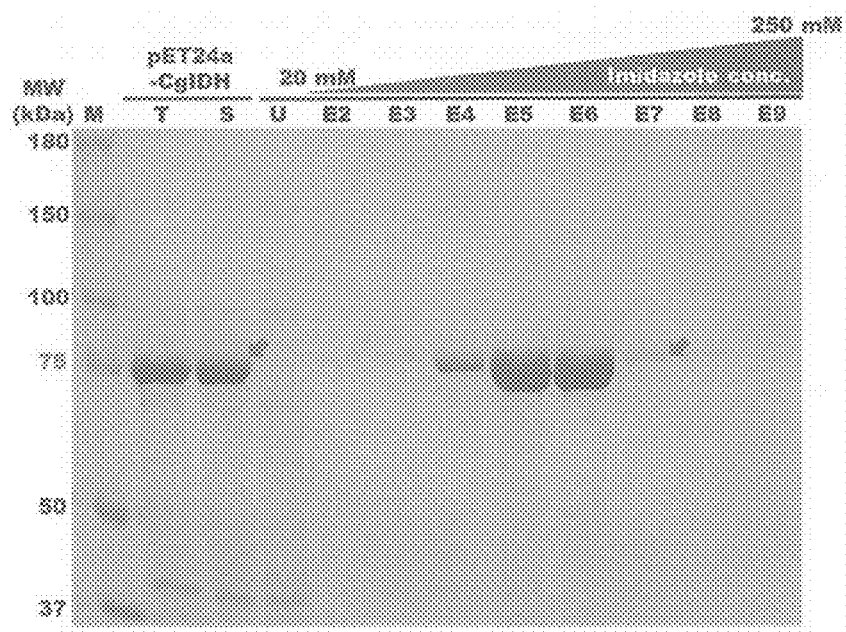
FIGS. 4A and 4B are each a SDS-PAGE analysis result that can confirm a pure separation and purification result of CgIDH and AvIDH.
Figure 4B:
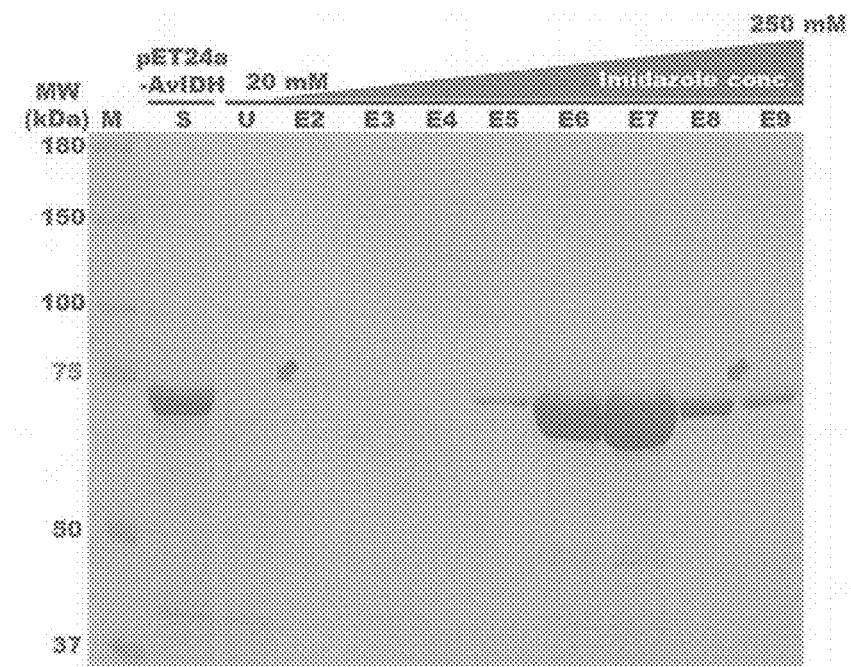

FIGS. 4A and 4B is a result of SDS-PAGE that can confirm a purification result of CgIDH and AvIDH using affinity chromatography. It was confirmed from FIGS. 4A and 4B that CgIDH was eluted at a concentration of about 40 to 60 mM imidazole, and AvIDH was eluted at a concentration of about 90 to 110 mM imidazole. In particular, it was confirmed that both of the eluted CgIDH and AvIDH were purified with a high purity of 95% or more.

Additionally, as a result of quantifying the protein of an eluted fraction by a protein quantification test (Bradford assay), it was confirmed that both recombinant proteins exhibited a purification yield of 1 g/L, indicating a high yield even in laboratory-level purification in which culture conditions were not optimized.

Example 3

Quaternary Structure of Purified Recombinant Protein

In order to confirm whether a multimer (quaternary structure) of the recombinant protein purified by the process as described above is formed, size exclusion chromatography was performed.

First, after CgIDH and AvIDH purified in Example 2 were each loaded onto a Superdex™ 200 10/300 GL column (GE Healthcare Life Science, USA), size exclusion chromatography was performed using 1×PBS (pH 7.4). Cytochrome P450 BM3 (blue, 119 kDa) was used as a control group, and conalbumin (purple, 75 kDa) and ovalbumin (orange, 45 kDa) were used as standard size markers. The results of performing size exclusion chromatography are shown in FIG. 5.

Figure 5:
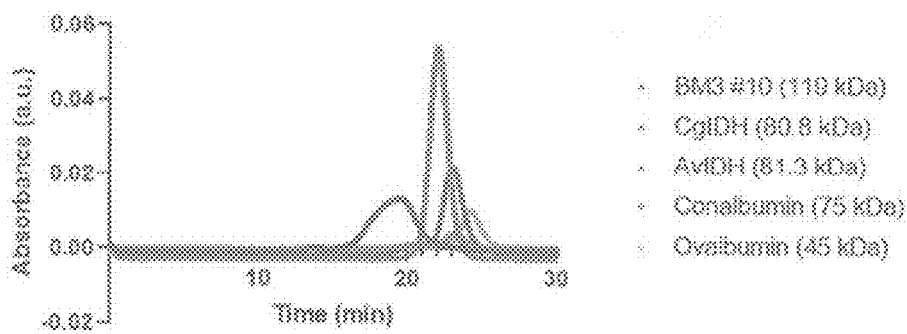
FIG. 5 is a size-exclusion chromatography analysis result of CgIDH and AvIDH.

It was confirmed from FIG. 5 that CgIDH and AvIDH were eluted at the peak position consistent with the SDS-PAGE analysis result, which means that both recombinant proteins have a monomeric form.

Example 4

Kinetic Constant Analysis of Purified Recombinant Protein

The analysis of kinetic properties related to an enzyme activity of the recombinant protein, that is, a kinetic constant, was performed by the following procedure.

The analysis of kinetic activity for each of the recombinant proteins purified in Example 2 was performed based on the method described in Chen, R. & Yang, H. Biochemistry and Biophysics, 383(2):238-245 (2000); and Watanabe, S. Microbiology 151(4):1083-1094 (2005).

Here, a $K_m$ (uM) value representing the affinity of the enzyme to the substrate as a reaction constant used in enzyme kinetics, a $K_{cat}$(S-1) value, which means the metabolic turnover number of the enzyme, and a $K_{cat}/K_m$ (S-1, M-1) value representing a reaction efficiency of the enzyme, were determined. The parameters of the wild-types CgIDH and AvIDH were used as control groups, and the results are shown in FIGS. 6A and 6B.

Figure 6A:
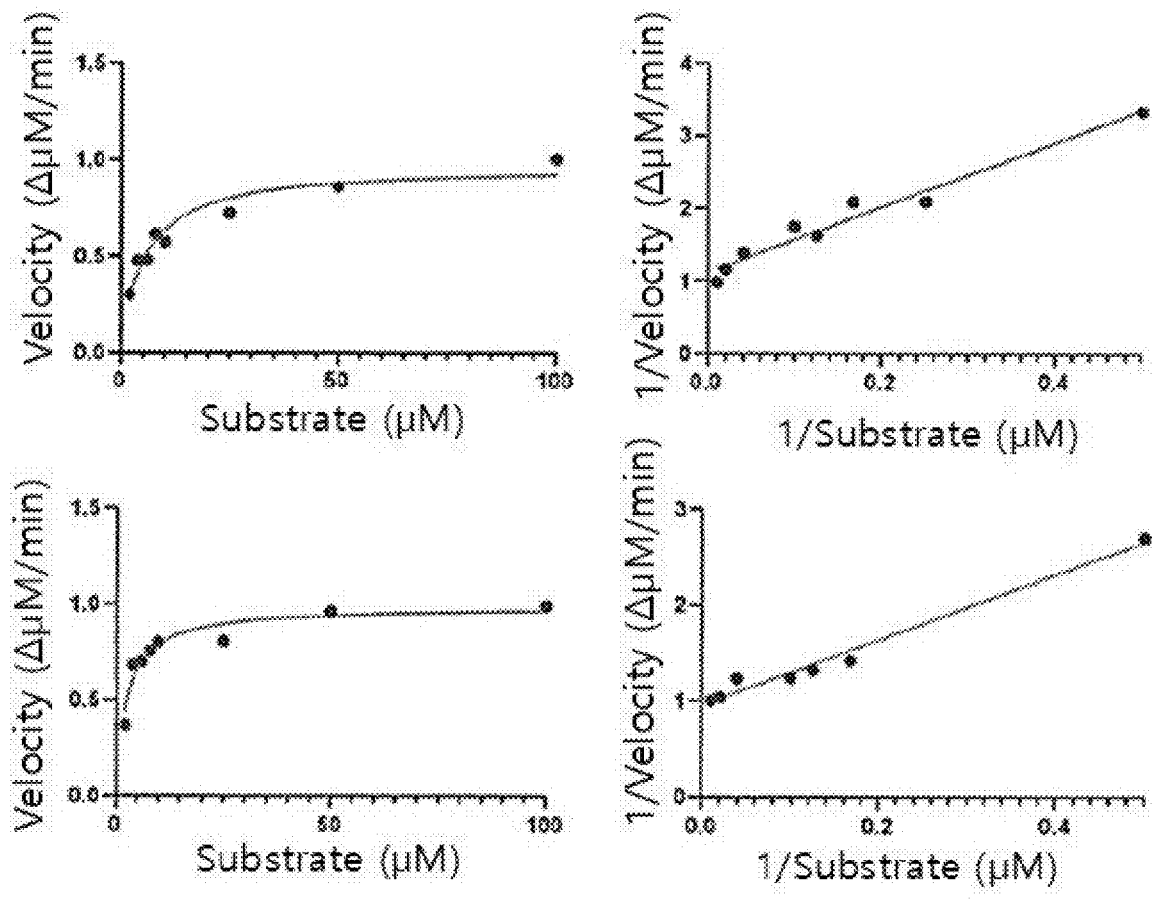
FIGS. 6A and 6B are an analysis result of the kinetic constants (Km and Vmax) of CgIDH and AvIDH.
Figure 6B:
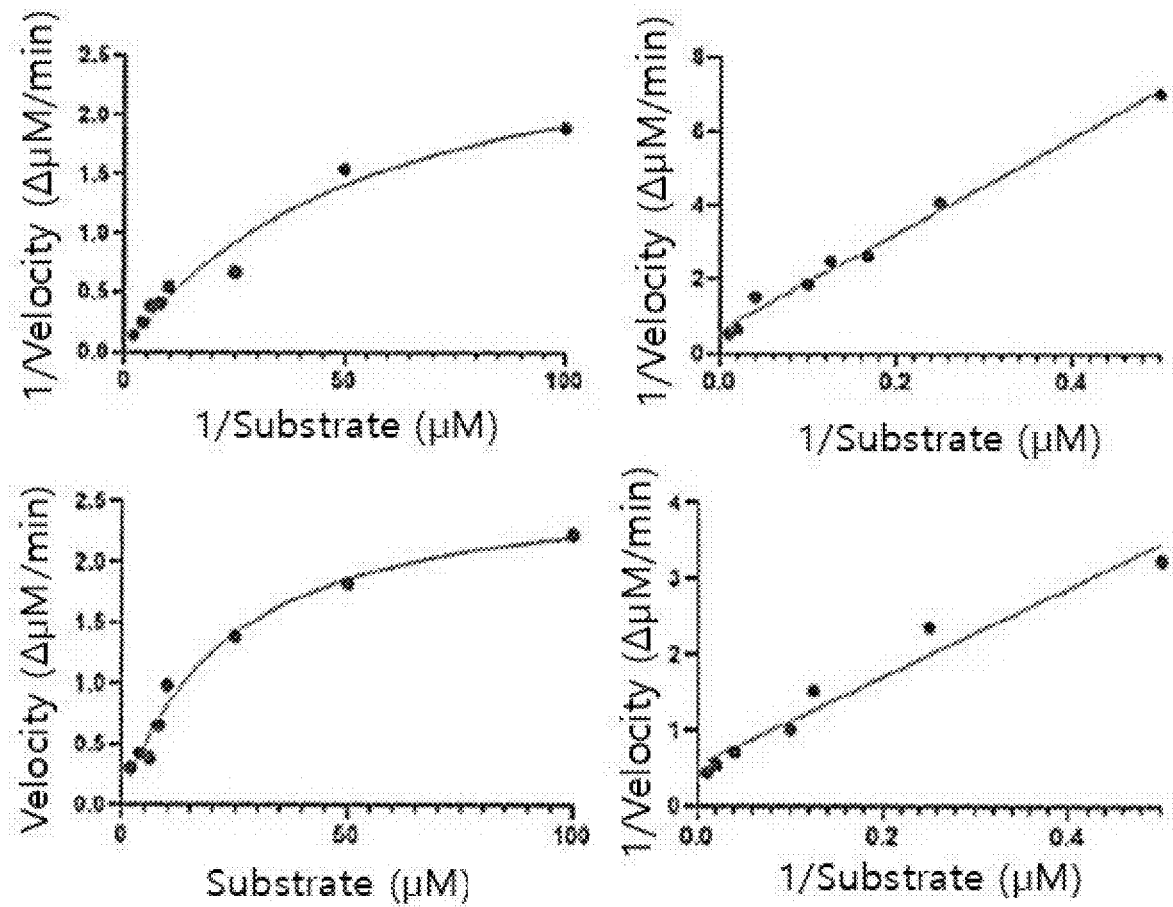

It was confirmed from FIGS. 6A and 6B that both CgIDH and AvIDH according to the present invention showed a slight decrease in $K_{cat}$ compared with the wild-types, but the enzyme activity for providing NADPH required for the reaction of the NADPH-dependent enzyme such as cytochrome P450 was sufficiently high.

Thus, the activity of the recombinant protein according to the present invention can be seen to be the same level as that of the wild-types, which supports the reliability of the result of the quaternary structure analysis of Example 3. That is, the above result can be interpreted as an indirect or considerable result indicating that there was no change in the quaternary structure during the producing process of the recombinant protein.

Example 5

Specific Activity Analysis of Recombinant Protein

In order to confirm the degree of NADPH regeneration by the activity of the IDH recombinant protein, CgIDH and AvIDH were each added to a reaction solution containing 100 mM potassium phosphate buffer (pH 7.4), 0.8 mM manganese sulfate ($MnSO_4$), 0.8 mM DL-isocitric acid, and 0.5 mM NADP+ so that the final concentrations were 5 nM, and the degree of increase of NADPH depending on the enzyme activity was measured with a spectrophotometer. When fluorescence was measured using a spectrophotometer, an excitation wavelength was set to 350 nm and an emission wavelength was set to 450 nm, and the measurement results are shown in FIG. 7.

Figure 7:
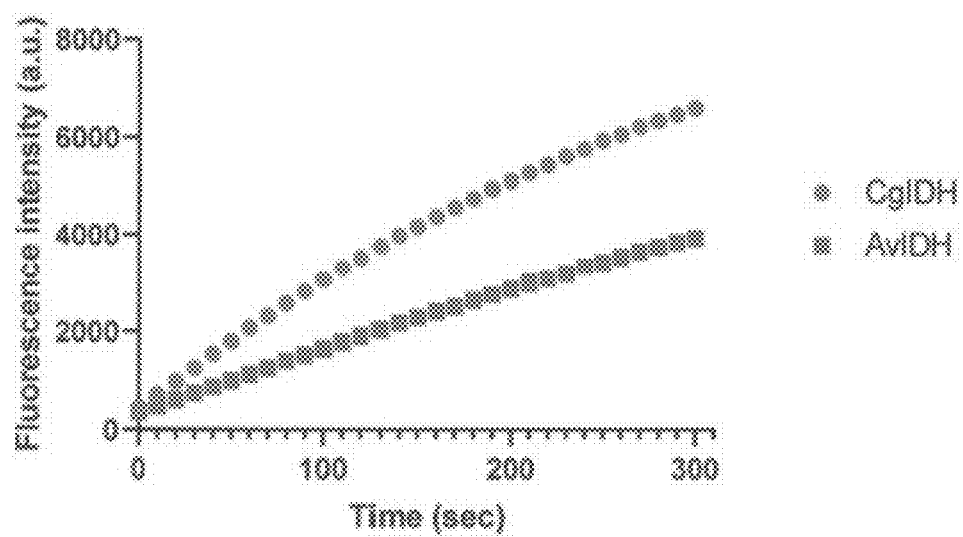
FIG. 7 is a measurement result of an enzyme activity of CgIDH and AvIDH.

It was confirmed from FIG. 7 that NADPH increased over time in each reaction solution containing each protein of CgIDH indicated by a circle and AvIDH indicated by a square, which suggests that both CgIDH and AvIDH generate NADPH by an enzymatic reaction that converts isocitric acid to α-ketoglutarate.

In addition, when the enzyme activity of the same amount of the recombinant protein is compared, a CgIDH enzyme reaction slope was found to be higher than that of an AvIDH enzyme reaction slope, which means that CgIDH has higher enzyme activity. These results are also consistent with those in FIGS. 6A and 6B of Example 4.

From the above results, it was confirmed that the specific activities of CgIDH and AvIDH correspond to 57 U/mg and 28 U/mg, respectively.

Example 6

Analysis of Coupling Reaction Between NADPH-Regeneration System Based on Isocitrate Dehydrogenase and Cytochrome P450 BM3

In order to confirm whether NADPH, which is the cofactor of the NADPH-dependent enzyme, can be continuously supplied, through the NADPH-regeneration system using the IDH recombinant protein, CgIDH and cytochrome P450 BM3 were added to a reaction solution containing 100 mM potassium phosphate buffer (pH 7.4), 0.8 mM manganese sulfate, 40 mM DL-isocitric acid, 0.5 mM NADP, and 2 mM omeprazole to prepare a reaction product, and the reaction product was prepared using AvIDH and cytochrome P450 BM3 in the same manner. Thereafter, coupling reactions between CgIDH and AvIDH, and cytochrome P450 BM3 were performed at 37° C. for each reaction to prepare the product.

NADPH Self-Fluorescence Analysis to Confirm Cofactor Regeneration

In the above process, 2 nM CgIDH and 500 nM cytochrome P450 BM3 were each added to the reaction solution at the final concentrations, and 2 nM AvIDH and 500 nM cytochrome P450 BM3 were each added to the reaction solution at the final concentration in the same manner. Thereafter, after each reactant was reacted at 37° C., whether or not NADPH was increased was measured using the spectrophotometer. When fluorescence was measured using the spectrophotometer, an excitation wavelength was set to 350 nm and an emission wavelength was set to 450 nm, and the measurement results are shown in FIGS. 8A and 8B.

Figure 8A:
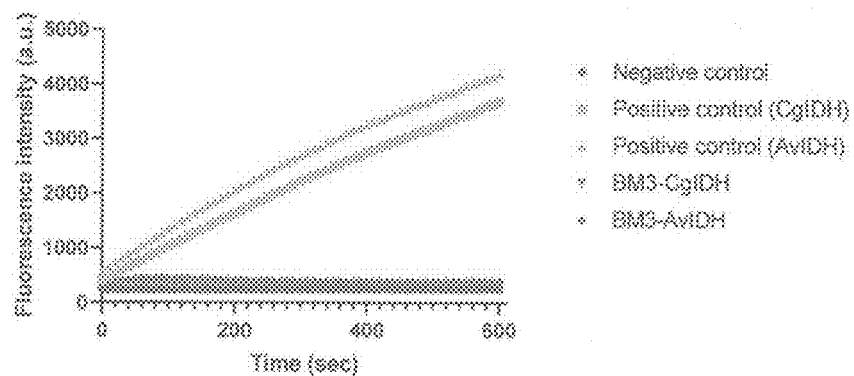
FIGS. 8A and 8B are graphs of results obtained by performing a coupling reaction between CgIDH or AvIDH and cytochrome P450 BM3, which is the NADPH-dependent enzyme, and performing an analysis with a spectrophotometer.

Here, the case in which the IDH recombinant protein was not added to the reaction solution was used as a negative control group (circle in FIG. 8A), and two cases in which cytochrome P450 BM3 was not added to the reaction solution were used as positive control groups (square and triangle in FIG. 8A).

Figure 8B:
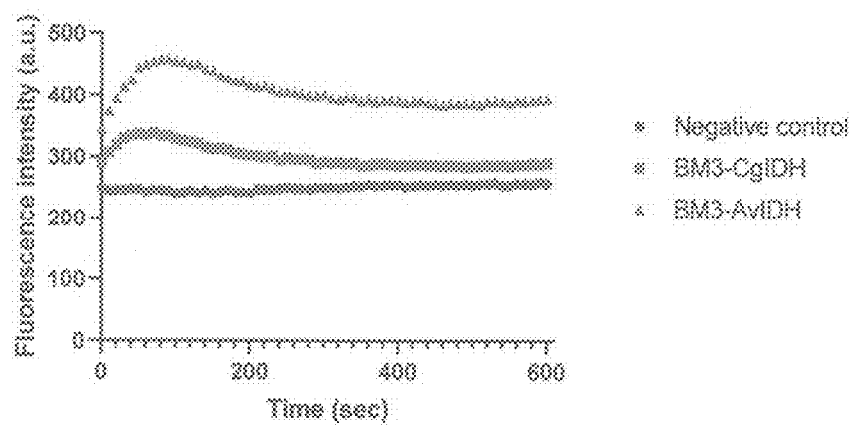

FIG. 8B illustrates fluorescence measurement results for two coupling reactions (CgIDH and cytochrome P450 BM3 (square); AvIDH and cytochrome P450 BM3 (triangle)) together with the negative control group (circle), wherein a fluorescence intensity scale on a vertical axis (y-axis) is set from 0 to 500 a.u. and is enlarged.

It was confirmed from FIGS. 8A and 8B that only in the case of the reaction solution in which both of the coupled proteins were present, the fluorescence intensity slightly increased due to NADPH generated by the IDH recombinant protein at the beginning of the reaction, but the fluorescence intensity remained at a certain level after a certain period of time, which suggests that NADPH produced by the IDH recombinant protein is consumed by cytochrome P450 BM3, which is the NADPH-dependent enzyme and NADP produced at the same time is again regenerated into NADPH by the IDH recombinant protein, thereby efficiently regenerating the cofactor, NADPH. A schematic representation of a reaction involving IDH recombinant protein, NADPH-dependent enzyme, NADP+, and NADPH in terms of regeneration of NADPH, is shown in Scheme 1 below:

$NADP^+ + $ IDH recombinant protein$\rightarrow$NADPH+NADPH-dependent enzyme$\rightarrow NADP^+$ 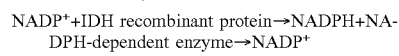 Scheme 1

Determination of Enzyme Concentration Ratio

In the above reaction, the amount of cytochrome P450 BM3 was high compared with the IDH recombinant protein, so NADPH was present in a small concentration in the reaction solution. Thus, in order to establish a more appropriate enzyme concentration ratio, 500 nM cytochrome P450 BM3 was added to a reaction solution containing 100 mM potassium phosphate buffer (pH 7.4), 0.8 mM manganese sulfate, 40 mM DL-isocitric acid, 0.5 mM NADP, and 2 mM omeprazole, and CgIDH and AvIDH were each added at 2 nM, 5 nM, and 10 nM (concentration ratio of 1:250, 1:100, 1:50, respectively) to prepare a reaction product. Thereafter, each reactant was subjected to a coupling reaction at 37° C., and then the degree of increase of NADPH was measured in the same manner. The results are shown in FIGS. 9A and 9B.

Figure 9A:
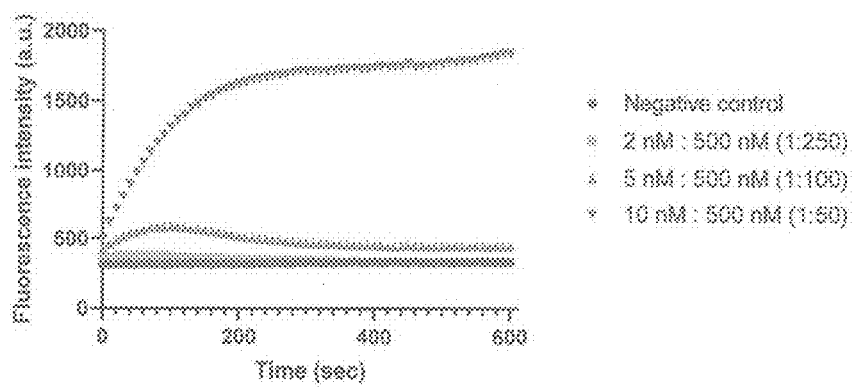
FIGS. 9A and 9B are graphs showing the degree of increase of NAPDH when determining an optimal enzyme concentration ratio for a coupling reaction between CgIDH or AvIDH and cytochrome P450 BM3.

FIG. 9A illustrates the result of the coupling reaction between CgIDH and cytochrome P450 BM3, wherein the concentration ratio of the two enzymes was set to 1:250 (square), 1:100 (triangle) and 1:50 (inverted triangle). In addition, FIG. 9B illustrates the result of the coupling reaction between AvIDH and cytochrome P450 BM3, wherein the concentration ratio of the two enzymes was set to 1:250 (square), 1:100 (triangle) and 1:50 (inverted triangle). In the same manner as in FIGS. 8A and 8B, the case in which the IDH recombinant protein was not added to the reaction solution was used as the negative control group (circle in FIGS. 9A and 9B).

Figure 9B:
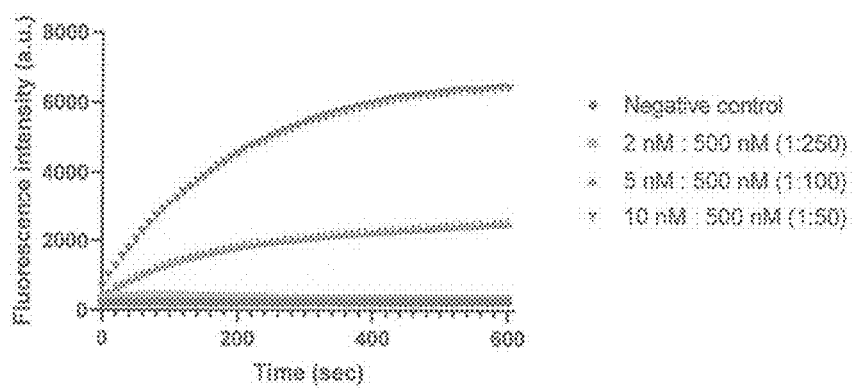
Figure 10A:
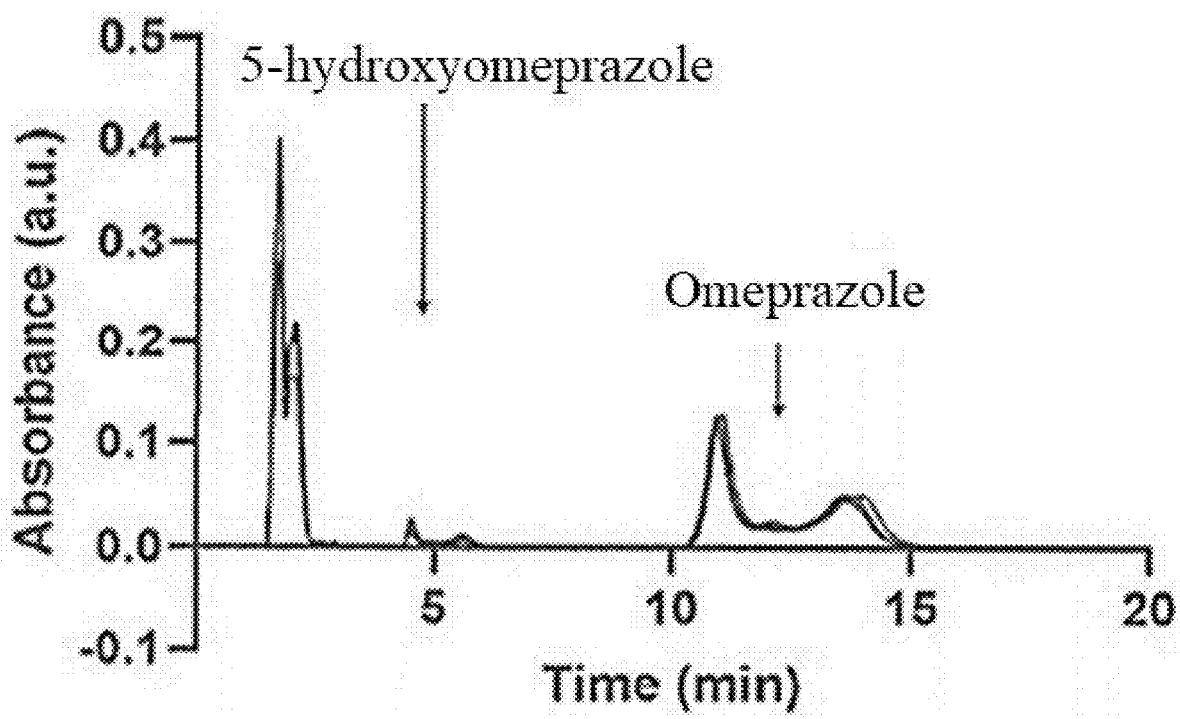
FIGS. 10A-10F are a series of HPLC analysis results of a hydroxylation reaction of a substrate by the coupling reaction between CgIDH or AvIDH and cytochrome P450 BM3.
Figure 10B:
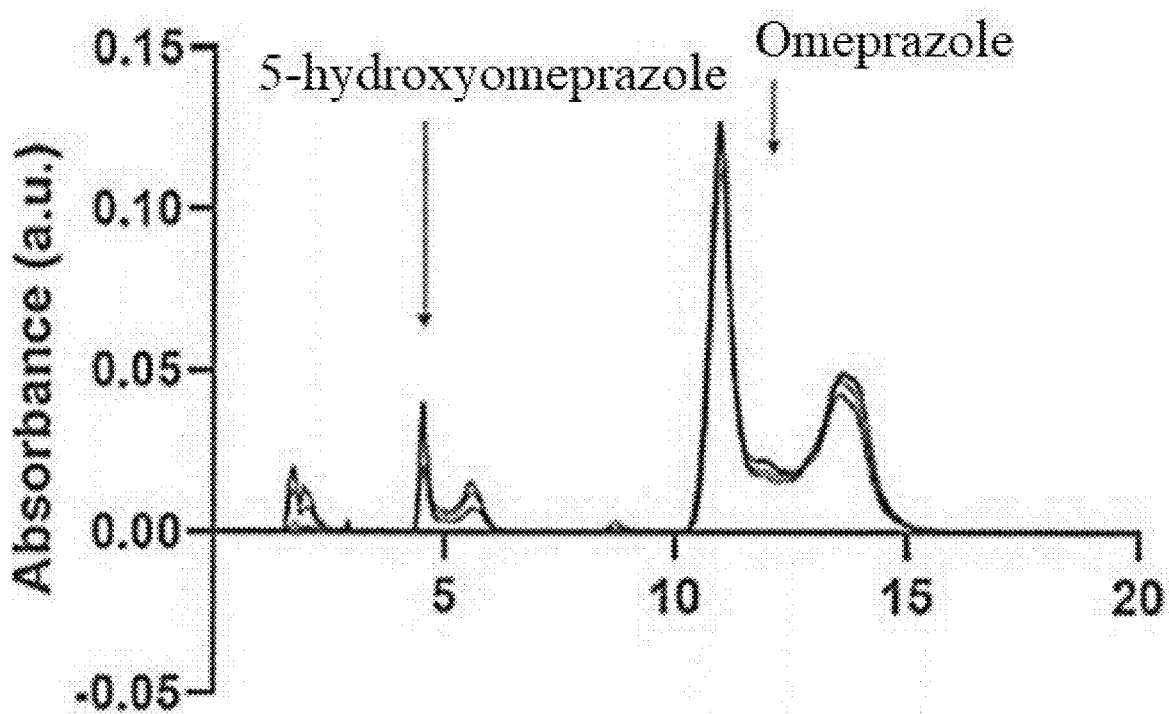
Figure 10C:
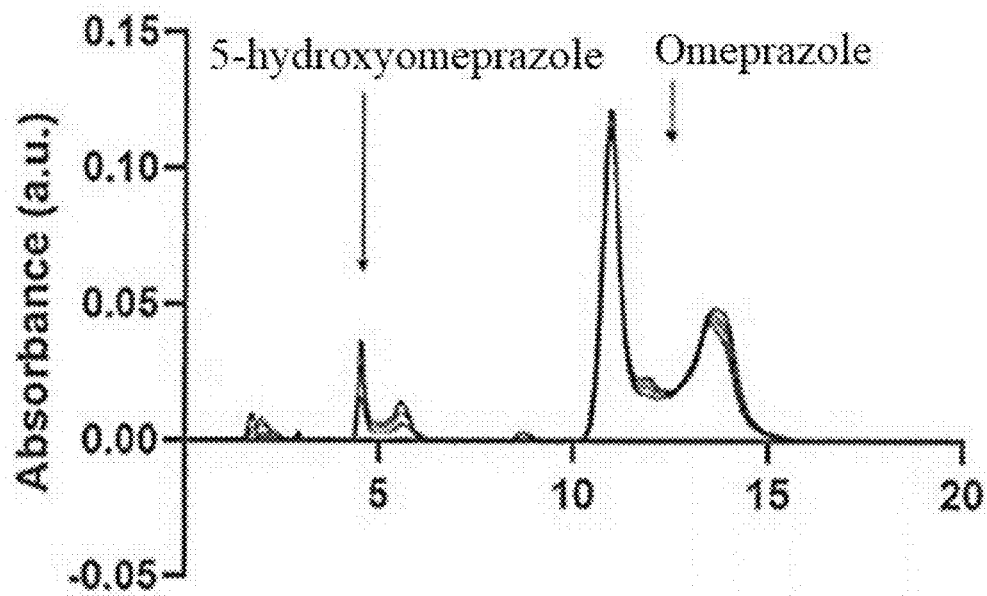
Figure 10D:
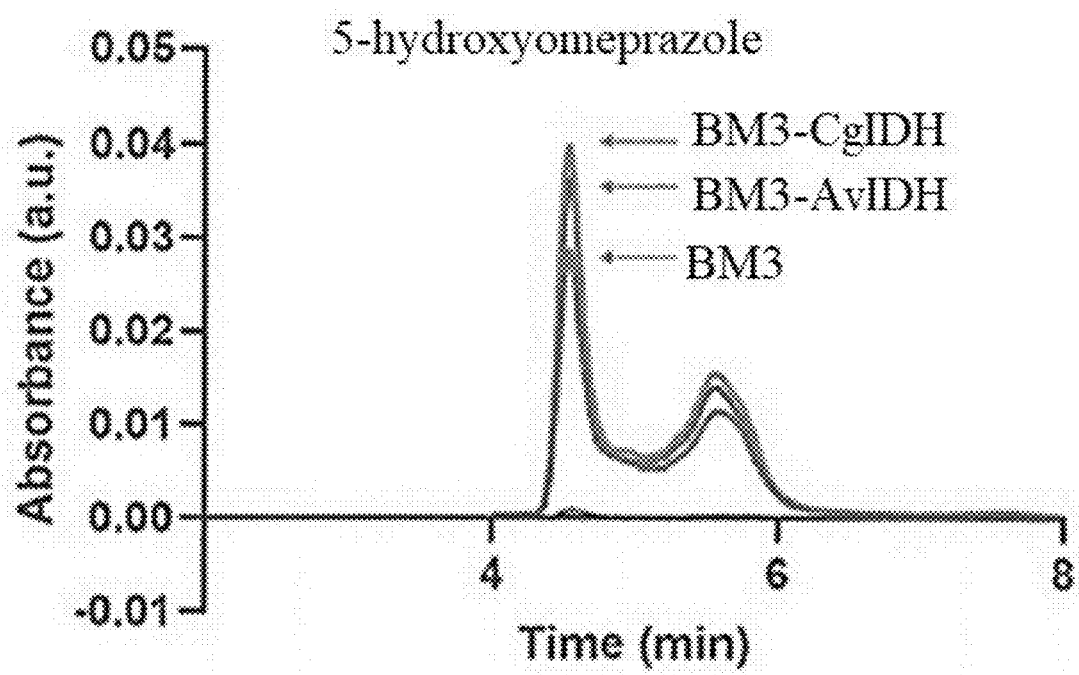
Figures 10E, 10F:
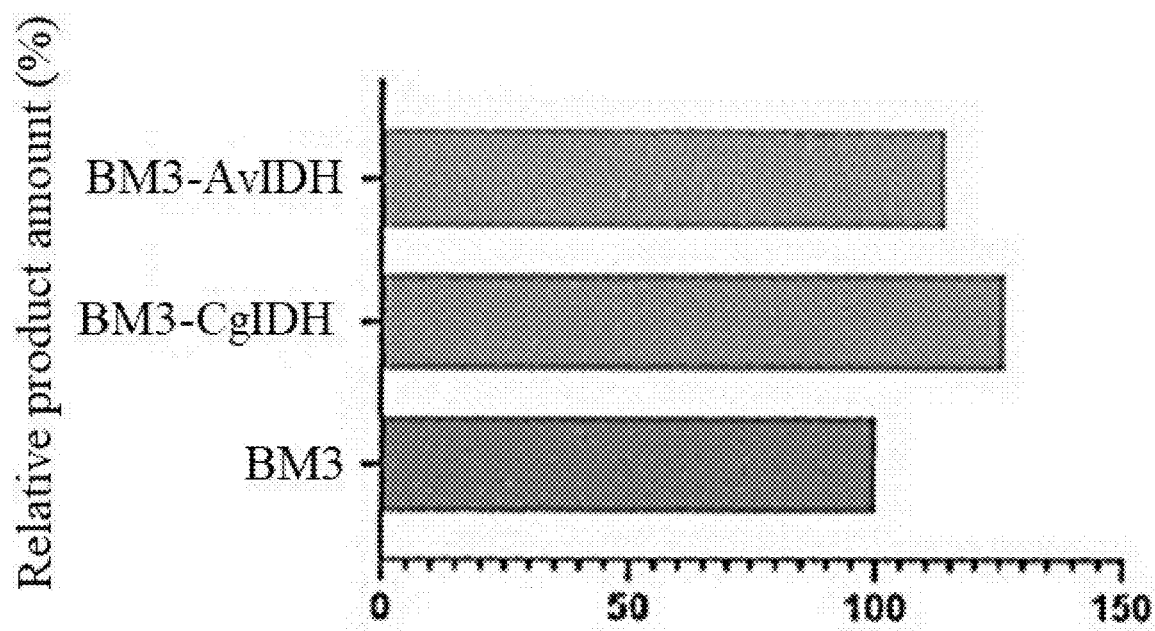

As can be seen from FIGS. 9A and 9B, an interval in which NADPH was maintained at a certain level was different depending on the concentration of CgIDH and AvIDH, and subsequent analysis was performed by setting the ratio of an enzyme concentration (for CgIDH, 1:50 and for AvIDH, 1:100) at which the fluorescence intensity was maintained at 2000 a.u. as the ratio of an appropriate enzyme concentration.

HPLC Analysis of Hydroxylation Product of Substrate

In the above reaction, in order to confirm that the activity of cytochrome P450 BM3 is maintained by substantial NADPH regeneration, and the hydroxylation reaction of omeprazole, which is one of the substrates, occurs, to 1 mL of a reaction solution containing 100 mM potassium phosphate buffer (pH 7.4), 0.8 mM manganese sulfate, 40 mM DL-isocitric acid, 0.5 mM NADP, and 2 mM omeprazole, CgIDH and cytochrome P450 BM3 were added so that the final concentrations were 10 nM and 500 nM, respectively, and AvIDH and cytochrome P450 BM3 were added so that the final concentrations were 5 nM and 500 nM, respectively, to prepare a reaction product.

The reaction mixture was recovered by 90 uL each time, mixed with 90 uL of methanol to stop the reaction, and then HPLC analysis was performed. Specific HPLC performance conditions are as follows:

HPLC was performed using an Alliance HPLC system (Waters).

A SunFire 18C column was used as a column

The amount of sample loading was set to 20 uL.

As a HPLC mobile phase, 30% acetonitrile was flowed at a flow rate of 1 mL/min, and an eluate was measured with ultraviolet (UV) light at 302 nm.

Analysis was performed using an Empower 3 (Waters) program.

Instead of using the NADPH-regeneration system as a control group, NADPH itself and a substrate were added to perform the hydroxylation reaction of the substrate through cytochrome P450 BM3 activity, and HPLC analysis was performed in the same manner. The results are shown in FIGS. 10A-10F.

It was confirmed from FIGS. 10A-10F that the product of the coupling reaction, that is, 5'-hydroxyomeprazole, which is a hydroxylated form of the substrate omeprazole, was eluted from all three reaction solutions (a coupling reaction between CgIDH and cytochrome P450 BM3, a coupling reaction between AvIDH and cytochrome P450 BM3, control) when five minutes has elapsed, and the shape of each peak was similar.

In addition, the elution amount of 5'-hydroxyomeprazole produced by the coupling reaction (5 min) with the NADPH-regeneration system of the present invention was measured to be 126% in the case of the coupling reaction between CgIDH and P450 BM3, and 114% in the case of the coupling reaction between AvIDH and P450 BM3, based on the elution amount of 5'-hydroxyomeprazole produced in the control group.

The above-mentioned elution amount suggests that the NADPH-regeneration system of the present invention may more effectively supply NADPH to the enzymatic reaction of the NADPH-dependent enzyme.

Example 7

Storage Stability of Recombinant Protein

In order to evaluate the stability of the recombinant protein produced in the present invention, after a certain period of time, each of the recombinant proteins stored at 4° C. was added to a reaction solution containing 100 mM potassium phosphate buffer (pH 7.4), 0.8 mM manganese sulfate, 40 mM DL-isocitric acid, and 0.5 mM NADP+ so that the final concentration was 5 nM, the reaction was proceeded as described in Example 5, and the degree of increase of NADPH was measured. The measurement results are shown in FIG. 11.

Figure 11:
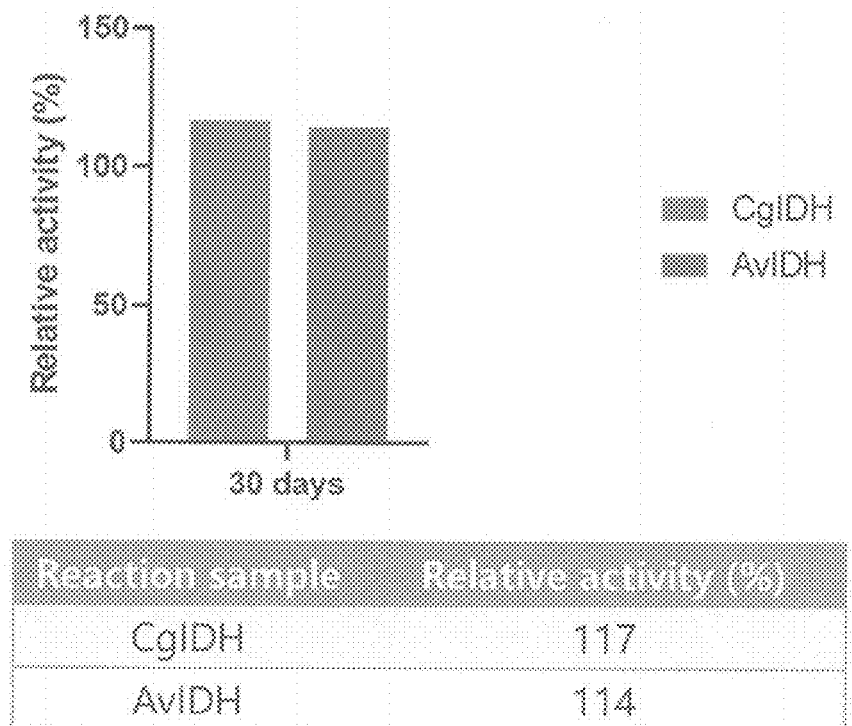
FIG. 11 is storage stability evaluation results of CgIDH and AvIDH.

It was confirmed from FIG. 11 that after storage at 4° C. for 30 days, the enzyme activity of the CgIDH and AvIDH recombinant proteins measured under the same conditions did not decrease.

In particular, it was confirmed that the activity increased by 10 to 20% compared with before storage, which suggests that the activity is maintained in the range of 90 to 110% of the initial activity, considering that a deviation occurs depending on reaction conditions and protein quantification.

That is, it was confirmed that the NADPH-regeneration system of the present invention may be stably utilized as an independent component for an NADPH-dependent enzymatic reaction, and may be applied as key parts by maintaining favorable stability for mass production and long-term storage in an NADPH-regeneration process for NADPH-dependent enzyme activity including cytochrome P450 BM3.

Example 8

Figure 12:
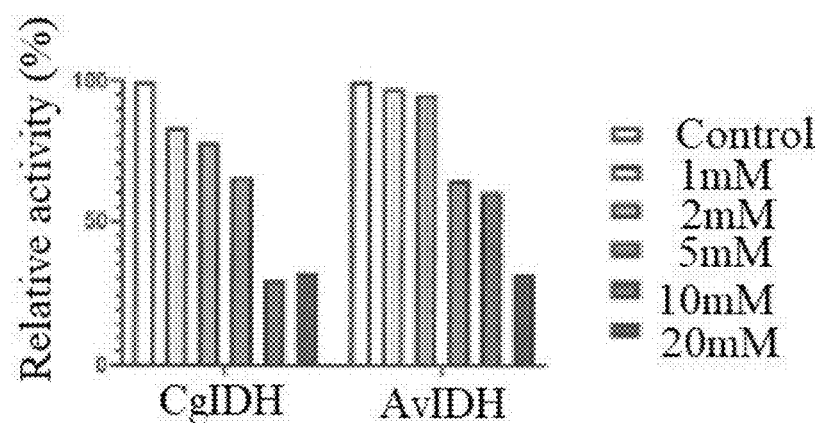
FIG. 12 is an evaluation result of an enzyme activity inhibitory effect by α-ketoglutarate, which is a reaction product of CgIDH and AvIDH recombinant proteins.

Enzyme Activity Inhibitory Effect Depending on Product of Recombinant IDH Protein In order to confirm an enzyme activity inhibitory effect by α-ketoglutarate, which is an enzyme reaction product of the recombinant protein produced in the present invention, a reaction product, in which 5 nM of CgIDH and 5 nM AvIDH were each added to a reaction solution containing 100 mM potassium phosphate buffer (pH 7.4), 0.8 mM manganese sulfate, 40 mM DL-isocitric acid, and 0.5 mM NADP, was prepared. Thereafter, α-ketoglutarate was added for each concentration to proceed the reaction as described in Example 5, and the degree of increase of NADPH was measured. The measurement results are shown in FIG. 12. Here, an experimental group to which α-ketoglutarate was not added was used as a control group.

It was confirmed from FIG. 12 that for CgIDH, the enzyme activity was reduced by 30% by the added 10 mM α-ketoglutarate, and for AvIDH, the enzyme activity was reduced by 30% by the added 20 mM α-ketoglutarate.

The above-mentioned reduction means that when the NADPH-regeneration system is operated in a batch process, an enzyme activity inhibition phenomenon may occur due to the enzyme reaction product, which suggests that it is preferable to perform a process of removing the enzyme reaction product by introducing a continuous process, a hollow tube membrane reactor, etc. in order to solve the above phenomenon. However, it was also confirmed that when the pH of the reaction process is corrected by adding a pH adjuster, etc., the inhibitory effect can be improved by 50% or more (results not attached).

Example 9

Analysis of Coupling Reaction Between NADPH-Regeneration System and Cytochrome P450 BM3 Depending on Substrate Change In Example 6, the substrate omeprazole was changed to omeprazole sulfide, ethoxycoumarin, and nitrophenol, respectively, and then NADPH-regeneration ability was analyzed under the same conditions.

As a result, the same substrate conversion result was confirmed even when the substrates other than omeprazole were used, which suggests that the NADPH-regeneration system using the IDH recombinant protein, regardless of the type of substrate, has the NADPH-regeneration ability to maintain NADPH-dependent enzyme activity. That is, it can be said that it is suitable as robust key parts of the NADPH-regeneration system.

Example 10

Analysis of Coupling Reaction Depending on Changes in NADPH-Regeneration System and NADPH-Dependent Enzyme In Example 6, after changing cytochrome P450, which is the NADPH-dependent enzyme, to mannitol 2-dehydrogenase, methylmalonate-semialdehyde dehydrogenase, glutamate dehydrogenase, and phenylalanine dehydrogenase, respectively, the NADPH-regeneration ability was analyzed under the same conditions.

As a result, the same results were confirmed for other types of NADPH-dependent enzymes other than cytochrome P450 BM3, which suggests that the NADPH-regeneration system using the IDH recombinant protein, regardless of the type of NADPH-dependent enzyme, has the NADPH regeneration ability to maintain NADPH-dependent enzyme activity. That is, it can be said that it is suitable as robust key parts of the NADPH-regeneration system.

Example 11

Whole Cell Reaction Analysis Through Co-Expression of Recombinant IDH Protein and Cytochrome P450

Transformants transformed with a plasmid in which the IDH recombinant protein according to the present invention and cytochrome P450 BM3 are co-expressed, were cultured as in the above Example, and 0.8 mM manganese sulfate, 2 mM omeprazole, a sufficient amount of potassium phosphate buffer (pH 7.4), DL-isocitric acid, and 0.5 mM NADP were added to a reaction solution with harvested cells after cultivation. Thereafter, HPLC analysis was performed in the same manner as in the above Example.

As a result, it was confirmed that 5'-hydroxyomeprazole was detected in reaction solution, which suggests that substrate conversion is possible even through a whole-cell reaction in which the NADPH-regeneration system using the IDH recombinant protein and the NADPH-dependent enzymes are simultaneously expressed.

Example 12

Whole Cell Reaction Analysis Through Fused Protein Expression of Recombinant IDH Protein with Cytochrome P450

Transformants transformed with a plasmid engineered so that the IDH recombinant protein according to the present invention and cytochrome P450 BM3 are expressed as a fusion protein in cells, were cultured as in the above Example. 0.8 mM manganese sulfate, 2 mM omeprazole, a sufficient amount of potassium phosphate buffer (pH 7.4), DL-isocitric acid, and 0.5 mM NADP were added to a reaction solution with harvested cells after cultivation. Thereafter, HPLC analysis was performed in the same manner as in the above Example.

As a result, it was confirmed that 5'-hydroxyomeprazole was produced by whole cell catalyst, which suggests that substrate conversion is possible even through the whole-cell reaction in which the NADPH-regeneration system using the IDH recombinant protein and the NADPH-dependent enzymes are expressed as a fusion protein.

The above results show that the difficulty of efficient regeneration of NADPH through the expression of fusion protein, which is one of the fundamental disadvantages of the conventional cytochrome P450 BM3 and the NADPH-regeneration system (e.g., G6PDH, etc), has been overcome, through the fusion protein expression of the NADPH-regeneration system using the IDH recombinant protein and the NADPH-dependent enzyme. In the future, the continuous reaction system with NADPH-regeneration part f, which fused the NADPH-dependent enzyme with IDH recombinant protein as a single protein, can be widely used in the development of new processes with excellent productivity.

The present invention relates to a recombinant vector including a polynucleotide encoding an isocitrate dehydrogenase recombinant protein from *Corynebacterium glutamicum* and an isocitrate dehydrogenase recombinant protein from *Azotobacter vinelandii*, a method for producing the recombinant protein, and an NADPH-regeneration system using the recombinant protein produced by the method. In the present invention, the enzyme in a monomeric form that may be efficiently used in the NADPH-regeneration system in the transformant into which the recombinant vector was introduced, was found, and the NADPH-regeneration system using the enzyme in a monomeric form has a very high utility value as biological parts and biocatalyst materials that provides NADPH to the NADPH-dependent enzyme.

Special portions of contents of the present invention have been described in detail herein above, and it will be obvious to those skilled in the art that this detailed description is only an exemplary embodiment and the scope of the present invention is not limited by this detailed description.

The invention claimed is:

1. A method of using a recombinant expression vector to regenerate NADPH comprising:
producing the recombinant expression vector comprising a polynucleotide encoding a monomeric isocitrate dehydrogenase (IDH) from *Corynebacterium glutamicum* or *Azotobacter vinelandii*;
producing a transformant transformed with the recombinant expression vector;
culturing the transformant to express the monomeric IDH;
recovering the soluble expressed monomeric IDH; and
coupling the recovered monomeric IDH to an NADPH-dependent enzyme,
wherein the transformant is *Escherichia coli*, wherein the monomeric IDH from *Corynebacterium glutamicum* consists of the amino acid sequence of SEQ ID NO: 1, and the monomeric IDH from *Azotobacter vinelandii* consists of the amino acid sequence of SEQ ID NO: 2.

2. The method of claim 1, wherein the recombinant expression vector further comprises a polynucleotide encoding the NADPH-dependent enzyme.

3. The method of claim 2, wherein the NADPH-dependent enzyme is selected from the group consisting of a dehydrogenase, a reductase, an oxidoreductase, a transhydrogenase, a peroxidase, an oxygenase, a monooxygenase, a flavodoxin, and a dehalogenase.

4. The method of claim 3, wherein the NADPH-dependent enzyme and the monomeric IDH are expressed as a single fusion protein.

5. The method of claim 1, further comprising linking the NADPH-dependent enzyme to the expressed monomeric IDH by a chemical linker.

6. The method of claim 5, wherein the chemical linker is selected from the group consisting of PEGylated bis(sulfosuccinimidyl) suberate (BS(PEG)5), PEGylated bis(sulfosuccinimidyl) suberate (BS(PEG)9), bis(sulfosuccinimidyl) glutarate-d0 (BS2G-d0), bis(sulfosuccinimidyl) 2,2,4,4-glutarate-d4 (BS2G-d4), disuccinimidyl dibutyric urea (DSBU), 1,5-difluoro-2,4-dinitrobenzene (DFDNB), dimethyl pimelimidate (DMP), dimethyl suberimidate (DMS), disuccinimidyl glutarate (DSG), dithiobis(succinimidyl) propionate (DSP), disuccinimidyl suberate (DSS), disuccinimidyl sulfoxide (DSSO), disuccinimidyl tartarate (DST), dimethyl-3,3-dithiobis propionimidate (DTBP), ethylene glycol bis(succinimidyl) succinate (EGS), tris-(succinimidyl) aminotriacetate (TSAT), and 1-ethyl-3-(3-dimethylaminopropyl) carbodiimide (EDC).

* * * * *

SEQUENCE LISTING

```
Sequence total quantity: 8
SEQ ID NO: 1         moltype = AA  length = 746
FEATURE              Location/Qualifiers
REGION               1..746
                     note = CgIDH protein
source               1..746
                     mol_type = protein
```

```
                        organism = synthetic construct
SEQUENCE: 1
MAKIIWTRTD EAPLLATYSL KPVVEAFAAT AGIEVETRDI SLAGRILAQF PERLTEDQKV      60
GNALAELGEL AKTPEANIIK LPNISASVPQ LKAAIKELQD QGYDIPELPD NATTDEEKDI     120
LARYNAVKGS AVNPVLREGN SDRRAPIAVK NFVKKFPHRM GEWSADSKTN VATMDANDFR     180
HNEKSIILDA ADEVQIKHIA ADGTETILKD SLKLLEGEVL DGTVLSAKAL DAFLLEQVAR     240
AKAEGILFSA HLKATMMKVS DPIIFGHVVR AYFADVFAQY GEQLLAAGLN GENGLAAILS     300
GLESLDNGEE IKAAFEKGLE DGPDLAMVNS ARGITNLHVP SDVIVDASMP AMIRTSGHMW     360
NKDDQEQDTL AIIPDSSYAG VYQTVIEDCR KNGAFDPTTM GTVPNVGLMA QKAEEYGSHD     420
KTFRIEADGV VQVVSSNGDV LIEHDVEAND IWRACQVKDA PIQDWVKLAV TRSRLSGMPA     480
VPFWLDPERAH DRNLASLVEK YLADHDTEGL DIQILSPVEA TQLSIDRIRR GEDTISVTGN     540
VLRDYNTDLF PILELGTSAK MLSVVPLMAG GGLFETGAGG SAPKHVQQVQ EENHLRWDSL     600
GEFLALAESF RHELNNNGNT KAGVLADALD KATEKLLNEE KSPSRKVGEI DNRGSHFWLT     660
KFWADELAAQ TEDADLAATF APVAEALNTG AADIDAALLA VQGGATDLGG YYSPNEEKLT     720
NIMRPVAQFN EIVDALKKLE HHHHHH                                         746

SEQ ID NO: 2              moltype = AA  length = 749
FEATURE                   Location/Qualifiers
REGION                    1..749
                          note = AvIDH protein
source                    1..749
                          mol_type = protein
                          organism = synthetic construct
SEQUENCE: 2
MSTPKIIYTL TDEAPALATY SLLPIIKAFT GSSGIAVETR DISLAGRLIA TFPEYLTDTQ      60
KISDDLAELG KLATTPDANI IKLPNISASV PQLKAAIKEL QQQGYKLPDY PEEPKTDTEK     120
DVKARYDKIK GSAVNPVLRE GNSDRRAPLS VKNYARKHPH KMGAWSADSK SHVAHMDNGD     180
FYGSEKAALI GAPGSVKIEL IAKDGSSTVL KAKTSVQAGE IIDSSVMSKN ALRNFIAAEI     240
EDAKKQGVLL SVHLKATMMK VSDPIMFGQI VSEFYKDALT KHAEVLKQIG FDVNNGIGDL     300
YARIKTLPEA KQKEIEADIQ AVYAQRPQLA MVNSDKGITN LHVPSDVIVD ASMPAMIRDS     360
GKMWGPDGKL HDTKAVIPDR CYAGVYQVVI EDCKQHGAFD PTTMGSVPNV GLMAQKAEEY     420
GSHDKTFQIP ADGVVRVTDE SGKLLLEQSV EAGDIWRMCQ AKDAPIQDWV KLAVNRARAT     480
NTPAVFWLDP ARAHDAQVIA KVERYLKDYD TSGLDIRILS PVEATRFSLA RIREGKDTIS     540
VTGNVLRDYL TDLFPIMELG TSAKMLSIVP LMSGGGLFET GAGGSAPKHV QQFLEEGYLR     600
WDSLGEFLAL AASLEHLGNA YKNPKALVLA STLDQATGKI LDNNKSPARK VGEIDNRGSH     660
FYLALYWQAA LAAQTEDKEL QAQFTGIAKA LTDNETKIVG ELAAAQGKPV DIAGYYHPNT     720
DLTSKAIRPS ATFNAALAPL ALEHHHHHH                                      749

SEQ ID NO: 3              moltype = DNA  length = 38
FEATURE                   Location/Qualifiers
misc_feature              1..38
                          note = CgIDH infusion F
source                    1..38
                          mol_type = other DNA
                          organism = synthetic construct
SEQUENCE: 3
gaaggagata tacatatggc taagatcatc tggacccg                             38

SEQ ID NO: 4              moltype = DNA  length = 42
FEATURE                   Location/Qualifiers
misc_feature              1..42
                          note = CgIDH infusion R
source                    1..42
                          mol_type = other DNA
                          organism = synthetic construct
SEQUENCE: 4
gtggtggtgg tgctcgagct tcttcagtgc gtcaacgatc tc                        42

SEQ ID NO: 5              moltype = DNA  length = 43
FEATURE                   Location/Qualifiers
misc_feature              1..43
                          note = AvIDH infusion F
source                    1..43
                          mol_type = other DNA
                          organism = synthetic construct
SEQUENCE: 5
gaaggagata tacatatgtc cacaccgaag attatctata cgc                       43

SEQ ID NO: 6              moltype = DNA  length = 37
FEATURE                   Location/Qualifiers
misc_feature              1..37
                          note = AvIDH infusion R
source                    1..37
                          mol_type = other DNA
                          organism = synthetic construct
SEQUENCE: 6
gtggtggtgg tgctcgagtg caagaggtgc cagagcc                              37

SEQ ID NO: 7              moltype = DNA  length = 2241
```

| FEATURE | Location/Qualifiers |
|---|---|
| misc_feature | 1..2241 |
| | note = CgIDH polynucleotide |
| source | 1..2241 |
| | mol_type = other DNA |
| | organism = synthetic construct |

SEQUENCE: 7

```
atggctaaga tcatctggac ccgcaccgac gaagcaccgc tgctcgcgac ctactcgctg    60
aagccggtcg tcgaggcatt tgctgctacc gcgggcattg aggtcgagac cgggacatt   120
tcactcgctg gacgcatcct cgcccagttc ccagagcgcc tcaccgaaga tcagaaggta   180
ggcaacgcac tcgcagaact cggcgagctt gctaagactc ctgaagcaaa catcattaag   240
cttccaaaca tctccgcttc tgttccacag ctcaaggctg ctattaagga actgcaggac   300
cagggctacg acatcccaga actgcctgat aacgccacca ccgacgagga aaaagacatc   360
ctcgcacgct acaacgctgt taagggttcc gctgtgaagc cagtgctgcg tgaaggcaac   420
tctgaccgcc gcgcaccaat cgctgtcaag aactttgtta agaagttccc cacaccgcatg   480
ggcgagtggt ctgcagattc caagaccaac gttgcaacca tggatgcaaa cgacttccgc   540
cacaacgaga agtccatcat cctcgacgct gctgatgaag ttcagatcaa gcacatcgca   600
gctgacgcca ccgagaccat cctcaaggac agcctcaagc ttcttgaagg cgaagttcta   660
gacggaaccg ttctgtccgc aaaggcactg gacgcattcc ttctcgagca ggtcgctcgc   720
gcaaaggcag aaggtatcct cttctccgca cacctgaagg ccaccatgat gaaggtctcc   780
gacccaatca tcttcggcca cgttgtgcgc gcttacttcg cagacgtttt cgcacagtac   840
ggtgagcagc tgctcgcagc tggcctcaac ggcgaaaacg gcctcgctgc aatcctctcc   900
ggcttggagt ccctggacaa cggcgaagaa atcaaggctg cattcgagaa gggcttggaa   960
gacgcccag acctggccat ggttaactcc gctcgcggca tcaccaacct gcatgtccct  1020
tccgatgtca tcgtggacgc ttccatgcca gcaatgattc gtacctccgg ccacatgtgg  1080
aacaaagacg accaggagca ggacaccctg gcaatcgactc ctctacgctg gcc        1140
gtctaccaga ccgttatcga agactgccgc aagaacggcg cattcgatcc aaccaccatg  1200
ggtaccgtcc ctaacgttgg tctgatggct cagaaggctg aagagtacgg ctccatgac   1260
aagaccttcc gcatcgaagc agacggtgtg gttcaggttg tttcctccaa cggcgacgtt  1320
ctcatcgac acgacgttga ggcaaatgac atctggcgtg catgccaggt caaggatgcc  1380
ccaatccagg attgggtaaa gcttgctgtc acccgctccc gtctctccgg aatgcctgca  1440
gtgttctggt tggatccaga gcgcgcacac gaccgcaacc tggcttccct cgttgagaag  1500
tacctggctc accacgacac cgagggcctg gacatccaga tcctccccc tgttgaggca  1560
acccgctct ccatcgaccg catccgccgt ggcgaggaca ccatctctgt caccggtaac  1620
gttctgcgtg actacaacac cgacctcttc ccaatcctgg agctgggcac ctctgcaaag  1680
atgctgtctg tcgttccttt gatggctggc ggcggactgt cgagaccgg tgctggtgga  1740
tctgctccta gcacgtcca gcaggttcag gaagaaaacc acctgcgttg ggattcctc   1800
ggtgagttcc tcgcactggc tgagtccttc cgccacgagc tcaacaacaa cggcaacacc  1860
aaggccggcg ttctggctga cgctctggac aaggcaactg agaagctgct gaacgaagag  1920
aagtccccat cccgcaaggt tggcgagatc gacaacgtg gctccactt ctggctgacc   1980
aagttctggg ctgacgagct cgctgctcag accgaggacg cagatctggc tgctaccttc  2040
gcaccagtcg cagaagcact gaacacaggc gctgcagaca tcgatgctgc actgctgcca  2100
gttcagggtg gagcaactga ccttgcgtggc tactactccc ctaacgagga gaagctcacc  2160
aacatcatgc gcccagtcgc acagttcaac gagatcgttg acgcactgaa gaagctcgag  2220
caccaccacc accaccactg a                                            2241
```

| SEQ ID NO: 8 | moltype = DNA length = 2250 |
|---|---|
| FEATURE | Location/Qualifiers |
| misc_feature | 1..2250 |
| | note = AvIDH polynucleotide |
| source | 1..2250 |
| | mol_type = other DNA |
| | organism = synthetic construct |

SEQUENCE: 8

```
atgtccacac cgaagattat ctatacgctc actgatgaag cacccgcact ggcgacttac    60
tctctgcttc ccatcatcaa agcgttcacc ggatcttcag gtatcgccgt tgaaacccgc   120
gatatctccc ttgcaggccg cctcatcgca accttccccg aatacctgac cgatacccag   180
aaaatctccg acgatttggc cgaactggga aaactggcca ccacgccgga cgccaacatc   240
atcaagctgc cgaactcag cgcctccgtc ccgcaactca aggccgccat caaggaactg   300
cagcacgcagg gctacaagct ccggactac cctgaagagc ccaagaccga caccgagaag   360
gacgtcaagg cccgctacga caagatcaag ggcagcgccg tgaacccgt cctgcgcgaa   420
ggcaactccg accgccgcgc gccactgtcc gtcaagaact acgccagaaa gcaccctcac   480
aagatgggcg cctggagtgc ggactccaag tcccatgtcg cccacatgga caacggtgat   540
ttctacggca gcgagaaggc cgctctgatt ggcgccccg gcagtgtgaa aatcgagctg   600
atcgccaaag acggcagcag cactgttctg aaggcaaaga cctctgttca ggctggcgag   660
atcatcgact cttcggtaat gagcaagaac gccttgcgca acttcatcgc cgctgaaatc   720
gaggatgcga agaagcaggg agtactgctg tccgtgcacc tgaaggcgac catgatgaag   780
gtgtccgacc ccatcatgtt cggccagatc gtctacaagg acagcctcacc   840
aagcacgcag aggtgctgaa cgatcggc ttcgacgtca acaatggcat cggtgatctc   900
tacgcccgga tcaagactct tcccgaagca aagcagaagg aaatcgaggc cgacatccag   960
gcggtttacg cccagcgccc gcaattggcg atggtgaact ccgacaaggg catcaccaac  1020
ctgcatgtgc cgagcgacgt catcgtcgac gcctcgatgc cggcgatgat ccgcgactcc  1080
ggcaagatgt ggggccccga cggcaagctg catgacacca aggcggtcat cccgaccgt   1140
tgctatgcg gcgtgtacca ggtggtcatc gaggactgca gcacgcacgg cacgcttcgac  1200
cccaccacca tggcagcgt gcccaacgtc ggttgatgg ctcagaaagc cgaggaatac   1260
ggctccacg acaagacctt ccagattcct gcagacggc tggtccgtgt gaccgatgaa  1320
agcggcaagc tcttgctgga gcaaagcgtg gaggccggcg acatttggcg catgtgccag   1380
gcgaaagacg ccccgatcca ggactgggtc aagctgccg tcaaccgcgc ccgcgccacc   1440
aatacccgg cggtgttctg gctggacccg gcgcgtgccc atgatgccca ggttattgcc   1500
```

```
aaggtcgagc gttacctgaa ggactacgat accagcggtc tcgacatccg catcttgtcg   1560
ccggtcgagg caacccgctt ctcgctggcc cgcatccgcg aaggcaagga caccatttcc   1620
gtcaccggca acgtcctgcg cgactacctg accgacctgt tcccgatcat ggaactgggt   1680
accagcgcca aaatgttgtc gatcgtcccg ctgatgagcg gcggcggtct gttcgaaacc   1740
ggcgcgggcg gctcggctcc caagcatgtc cagcagttcc tcgaggaagg ttacctgcgt   1800
tgggattcgc tcggcgagtt cctcgctctt gccgcatccc tggagcactt gggcaacgcc   1860
tacaagaacc cgaaagcgct tgtcctggcc agcaccctgg accaggctac cggcaagatt   1920
ctcgataaca acaaatcgcc ggcacgtaag gttggcgaga tcgataaccg cggtagccac   1980
ttctacttgg cactctactg ggcccaggca ttggcagcgc aaaccgagga caaggaactg   2040
caagcccagt tcaccggcat tgccaaggct ctgaccgaca acgagaccaa gatcgtcggc   2100
gagttggctg cagcccaagg caagcctgtg gatatcgctg gctactacca tccgaatacc   2160
gacctgacca gcaaggccat ccgcccgagc gctactttca acgcggctct ggcacctctt   2220
gcactcgagc accaccacca ccaccactga                                    2250
```